US005846802A

United States Patent [19]
Buxton et al.

[11] Patent Number: 5,846,802
[45] Date of Patent: *Dec. 8, 1998

[54] FUNGAL PROTEASE

[76] Inventors: Frank Buxton, Holderstüdeliweg 32, 4132 Muttenz, Switzerland; Albert Hinnen, Am Planetarium 32, 07743 Jena, Germany; Jacob Visser, Hinkeloordseweg 5, 6703 CK Wgeningen, Netherlands

[*] Notice: The terminal 3 months of this patent has been disclaimed.

[21] Appl. No.: 225,488

[22] Filed: Apr. 8, 1994

Related U.S. Application Data

[63] Continuation-in-part of Ser. No. 47,214, Apr. 13, 1993, abandoned.

[30]     Foreign Application Priority Data

Apr. 15, 1992  [GB]  United Kingdom ............... 9281028l.3
Mar. 12, 1993  [GB]  United Kingdom ................ 9305097.9

[51] Int. Cl.$^6$ ........................... C12N 15/57; C12N 15/80; C12N 19/34; C12N 9/12
[52] U.S. Cl. ........................ 435/225; 435/69.1; 435/91.1; 435/254.11; 435/254.3; 435/320.1; 435/14; 435/28; 435/68; 536/23.2
[58] Field of Search .................................... 435/225, 69.1, 435/172.3, 252.3, 254.3, 320.1; 536/252.3, 23.2

[56]              References Cited

U.S. PATENT DOCUMENTS

| 4,885,249 | 12/1989 | Buxton et al. ........................ 435/172.3 |
| 4,943,529 | 7/1990 | Van Den Berg et al. ........... 435/172.3 |
| 5,077,204 | 12/1991 | Brake et al. ............................ 435/68.1 |
| 5,162,220 | 11/1992 | Oshima et al. .......................... 435/224 |
| 5,460,950 | 10/1995 | Barr et al. .............................. 435/69.1 |

FOREIGN PATENT DOCUMENTS

WO 90/00192  1/1992  WIPO .

OTHER PUBLICATIONS

Sakka, K., et al., Journal of Fermentation Technology, vol. 63, No. 5, "Purification and some properties of a serine proteinase from a mutant of *Aspergillus niger*" pp. 479–483, 1985.
Barthomeuf, C., et al., Chemical Pharmacutical Bulletin, vol. 37, No. 5, "Properties of a new alkaline proteinase from *Aspergillus niger*", pp. 1333–1336, 1989.
Barthomeuf, C., et al., Journal of Fermentation and Bioengineering, vol. 73, No. 3, "Collagenolytic activity of a new semi–alkaline protease from *Aspergillus niger*", pp. 233–236, 1992.
Kregar, I., et al., Symposia Biologica Hungarica, vol. 25, "Acid proteinases of microbial origin", pp. 425–434, 1984.
Barthomeuf et al., "Isolation and Purification of a New Protease from *Aspergillus niger* LCG N° 9", *Biotech. Tech.*, 2(1):29–34 (1988).
Barthomeuf et al., "Properties of a New Alkaline Proteinase from *Aspergillus niger*", *Chem. Pharm. Bull.*, 37(5):1333–1336 (1989).

Berka et al., "Molecular cloning and deletion of the gene encoding aspergillopepsin A from *Aspergillus awamori*", *Gene*, 86:153–162 (1990).
Bosmann et al., "Protein Catabolism. II. Identification of Neutral and Acidic Proteolytic Enzymes in *Aspergillus niger*", *Biochim. Biophys. Acta*, 293:476–489 (1973).
Chopra et al., "Influence of Various Nitrogen and Carbon Sources on the Production of Pectolytic, Cellulolytic Enzymes by *Aspergillus niger*", *Folia Microbiol.* 30:117–125 (1985).
Degan et al., "Purification and Characterization of Two Serine Carboxypeptidases from *Aspergillus niger* and Their Use in C–Terminal sequencing of Proteins and Peptide Synthesis", *Applied and Environment Microbiology*, 58(7):2144–2152 (1992).
Dunn–Coleman et al., "Commerical Levels of Chymosin Production by Aspergillus", *Biotechnology*, 9:976–981 (1991).
Durham et al., "Novel Alkaline– and Heat–Stable Serine Proteases from Alkalophilic Bacillus sp. Strain GX6638", *J. Bacteriology*, 169(6):2762–2768 (1987).
Frederick et al., "Distant upstream regulatory sequences control the level of expression of the am (GDH) locus of *Neurospora crassa*", *Curr Genet* 18:53–58 (1990).
Frederick et al., "Cloning and characterisation of pepC, a gene encoding a serine protease from *Aspergillus niger*", *Gene*, 125:57–64 (1993).
Gunkel et al., "Proteinase K from *Tritiachium album* Limber", *Eur. J. Biochem.*, 179:185–194 (1989).
Habener et al., "5–Flurodeoxyuridine as an alternative to the synthesis of mixed hybridization probes for the detection of specific gene sequences", *Proc. Natl. Acad. Sci.*, 85:1735–1739 (1988).
Ichishima et al., "Purification and Characterization of a New Type of Acid Carboxypeptidase from Aspergillus", *Biochim. Biophys. Acta*, 258:274–288 (1972).
Inoue et al., "The Gene and Deduced Protein Sequences of the Zymogen of *Aspergillus niger* Acid Proteinase A", *J. Biol. Chem.*, 266(29):19484–19489 (1991).
Isogai et al., "Cloning and Nucleotide Sequences of the Complementary and Genomic DNAs for the Alkaline Protease from *Acremonium chrysogenum*", *Agric. Biol. Chem.*, 55(2):471–477 (1991).
Jany et al., "Amino acid sequence of proteinase K from the mold *Tritirachium album* Limber", *FEBS Lett.*, 199(2):139–144 (1986).

(List continued on next page.)

*Primary Examiner*—Robert A. Wax
*Assistant Examiner*—William W. Moore
*Attorney, Agent, or Firm*—Gregory D. Ferraro

[57]              ABSTRACT

The present invention concerns a novel DNA sequence coding for an Aspergillus serine protease of the subtilisin-type, an Aspergillus serine protease of the subtilisin-type per se and a method for the preparation thereof. The invention further concerns a novel Aspergillus mutant strain defective in a serine protease of the subtilisin-type, which is useful for the expression of heterologous protein, and a method for the preparation of such a mutant strain.

13 Claims, No Drawings

OTHER PUBLICATIONS

Jaton–Ogay et al., "Nucleotide sequence of the genomic and a cDNA clone encoding an extracellular alkaline protease of *Aspergillus fumigatus*", *FEMS Microbiology Letters*, 92:163–168 (1992).

Krishnan et al., "Purification of an acid protease and a serine carboxypeptidase from *Aspergillus niger* using metal–chelate affinity chromatography", *J. of Chromatography*, 329:165–170 (1985).

Krishnan et al. "Purification and Some Properties of Three Serine Carboxypeptidase from *Aspergillus niger*", *J. of Chromatography*, 370:315–326 (1986).

Kumagai et al., "Isolation, Purification and Some Chemical Properties of an Acid Carboxypeptidase from *Aspergillus niger var. macrosporus* ", *Biochim. Biophys. Acta*, 659:334–343 (1981).

Matsushima et al., "High alkaline protease–yielding mutants of *Aspergillus niger* induced by ultraviolet irradiation", *Chemical Abstracts*, 73(13):Abs. No. 6305050 (1967).

Mattern et al., "Isolation and characterization of mutants of *Aspergillus niger* deficient in extracellular protease", *Mol. Gen. Genet*, 234:332–336 (1992).

Moehle et al., "Protease B of the Lysosomelike Vacuole of the Yeast *Saccharomyces cerevisiae* Is Homologous to the Subtilisin Family of Serine Proteases", *Molec. Cell. Biol.*, 7(1):4390–4399 (1987).

Monod et al., "Virulence of alkaline protease–defidient mutants of *Aspergillus fumigatus*", *FEMS Microbiology Letters*, 106:39–46 (1993).

Ogawa et al., "Secretion of *Aspergillus oryae* Alkaline Protease in an Osmophilic Yeast, *Zygosaccharomyces rouxii*", *Agric. Biol. Chem.*, 54(10):2521–2529 (1990).

Pourrat et al., "Production of Semi–Alkaline Protease by *Aspergillus niger*", *J. Ferment. Technol.*, 66(4):383–388 (1988).

Sakka et al., "Purification and Some Properties of Serine Proteinase from a Mutant of *Aspergillus niger*", *J. Ferment. Technol.*, 63(5):479–483 (1985).

Samal et al., "Cloning and expression of the gene encoding a novel proteinase from *Tritiachium album* Limber", *Gene*, 85:329–333 (1989).

Samal et al., "Isolation and characterization of the gene encoding a novel, thermostable serine proteinase from the mould *Tritrachium album* Limber", *Molec. Microbiol.*, 4(10):1789–1792 (1990).

Siezen et al., "Homology modeling and protein engineering strategy of subtilases, the family of subtilisin–like serine proteinases", *Protein Engineering*, 4(7):719–737 (1991).

Takahashi et al., "The Primary Structure of *Aspergillus niger* Acid Proteinase A", *J. Biol. Chem.*, 266(29):19480–19483 (1991).

Tatsumi et al., "Cloning and Sequencing of the Alkaline Protease cDNA from *Aspergillus oryae*", *Agric. Biol. Chem.*, 52(7):1887–1888 (1988).

Tatsumi et al., "A full length of cDNA clone for the alkaline protease from *Aspergillus oryzae*: Structural analysis and expression in *Saccharomyces cerevisiae*", *Mol. Gen. Genet*, 219:33–38 (1989).

Tatsumi et al., "Cloning and expression in yeast of a cDNA clone encoding *Aspergillus oryzae* neutral protease II, a unique metalloprotease", *Mol. Gen. Genet.*, 228:97–103 (1991).

Wells et al., "Subtilisin—an enzyme design to be engineered", *TIBS Trends in Biochemical Sciences*, 13:291–297 (1988).

Wolf et al., "Studies on a Proteinase B Mutant of Yeast", *Eur. J. Biochem.*, 98:375–384 (1979).

Yelton et al., "Transformaton of *Aspergillus nidulans* by using a trpC plasmid", *Proc. Natl. Acad. Sci. USA*, 81:1470–1474 (1984).

SEQUENCE LISTING ( 1 ) GENERAL INFORMATION:

( i i i ) NUMBER OF SEQUENCES: 18

( 2 ) INFORMATION FOR SEQ ID NO:1:

(i) SEQUENCE CHARACTERISTICS:
    (A) LENGTH: 3220 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Aspergillus niger
    (B) STRAIN: N400

(vii) IMMEDIATE SOURCE:
    (B) CLONE: pTZPEPC (ix) FEATURE:
    (A) NAME/KEY: promoter
    (B) LOCATION: 1..377

(ix) FEATURE:
    (A) NAME/KEY: sig_peptide
    (B) LOCATION: 378..435

(ix) FEATURE:
    (A) NAME/KEY: intron
    (B) LOCATION: 757..826

(ix) FEATURE:
    (A) NAME/KEY: CDS
    (B) LOCATION: join(388..756, 827..2059)
    (D) OTHER INFORMATION: /note= "subtilisin-type protease;
        PEPC of Aspergillus niger; product of pepC gene"

(xi) SEQUENCE DESCRIPTION: SEQ ID NO:1:

```
GGATCCATCC ATTCACTCAG CTTTCCTTGT CGGTGGACTG TCGAGTCTAC CCCAGGTCCC        60

AGTTTCTCCG ACCGCGCTAA TCGGGGGCTA TCGACAACCA GTGATTCTGC TGTGTCATCC       120

GGGCGTATGG CGTAAATTAC CGTATGCCGG TTGCATCATC ACCTGCTGCC CTTGCCTCTT       180

GCTGAATACC GTCCGCCATC CATCTGTCCT CCTCTCCCTC TCTCTTCATC TCCAACCTCC       240

CCTTCCTCCT CCCTCCCTCC TTCTCTTCAT CTTTATCTTG ACCTATTTCC ATCTTTCTCA       300

TCTCTCAGTT GTTTCAATCT CTTGTACACG CCCTACTCAC TCTCCTTTTC ACCGGGCTGC       360

TGTGGGTTCC GTCTTAAGCT ATCCATC ATG AAG GGC ATC CTC GGC CTT TCC          411
                               Met Lys Gly Ile Leu Gly Leu Ser
                                 1               5

CTC CTC CCG TTG CTG ACG GCT GCG TCG CCC GTC TTC GTT GAC TCC ATC         459
Leu Leu Pro Leu Leu Thr Ala Ala Ser Pro Val Phe Val Asp Ser Ile
        10                  15                  20

CAT AAT GAA GCT GCC CCC ATC TTG TCT GCT ACC AAC GCG AAG GAG GTT         507
His Asn Glu Ala Ala Pro Ile Leu Ser Ala Thr Asn Ala Lys Glu Val
 25                  30                  35                  40

CCC GAC TCC TAC ATC GTC GTT TTC AAG AAG CAC GTC ACT TCA GAG CTG         555
Pro Asp Ser Tyr Ile Val Val Phe Lys Lys His Val Thr Ser Glu Leu
                 45                  50                  55

GCT TCG GCT CAC CAC AGC TGG GTG CAG GAC ATC CAT GAC TCT CAG AGC         603
Ala Ser Ala His His Ser Trp Val Gln Asp Ile His Asp Ser Gln Ser
             60                  65                  70

GAG CGG ACT GAG CTG AAG AAG CGG TCG CTC TTC GGC CTT GGG GAC GAG         651
Glu Arg Thr Glu Leu Lys Lys Arg Ser Leu Phe Gly Leu Gly Asp Glu
         75                  80                  85

GTC TAT CTG GGT CTC AAG AAC ACC TTT GAC ATT GCT GGT TCT CTG ATC         699
Val Tyr Leu Gly Leu Lys Asn Thr Phe Asp Ile Ala Gly Ser Leu Ile
     90                  95                 100
```

| | | | | | | | | | | | | | | | | |
|---|---|---|---|---|---|---|---|---|---|---|---|---|---|---|---|---|
| GGT | TAC | TCT | GGT | CAC | TTC | CAC | GAG | GAT | GTC | ATC | GAG | CAA | GTC | CGC | AGA | 747 |
| Gly | Tyr | Ser | Gly | His | Phe | His | Glu | Asp | Val | Ile | Glu | Gln | Val | Arg | Arg | |
| 105 | | | | 110 | | | | | 115 | | | | | | 120 | |

| | | | | |
|---|---|---|---|---|
| CAC | CCC | GAT | GTGAGTTACA  CCCCTATCT  AAGCATCCCT  CGTTATCTCT | 796 |
| His | Pro | Asp | | |

| | | | | | | | | |
|---|---|---|---|---|---|---|---|---|
| AAGATAAGCT  TCTAACATCG  GTCAATGTAG | GTC | GAT | TAC | ATC | GAG | CGG | GAT | TCC | 850 |
| | Val | Asp | Tyr | Ile | Glu | Arg | Asp | Ser | |
| | | | 125 | | | | | 130 | |

| | | | | | | | | | | | | | | |
|---|---|---|---|---|---|---|---|---|---|---|---|---|---|---|
| GAA | GTT | CAC | ACC | ATG | GAA | GGG | GCC | ACC | GAA | AAG | AAC | GCC | CCT | TGG | GGT | 898 |
| Glu | Val | His | Thr | Met | Glu | Gly | Ala | Thr | Glu | Lys | Asn | Ala | Pro | Trp | Gly |
| | | | | 135 | | | | | 140 | | | | | 145 | |

| | | | | | | | | | | | | | | | | |
|---|---|---|---|---|---|---|---|---|---|---|---|---|---|---|---|---|
| CTG | GCT | CGT | ATC | TCT | CAC | CGT | GAT | AGC | CTG | ACC | TTC | GGT | AAC | TTC | AAC | 946 |
| Leu | Ala | Arg | Ile | Ser | His | Arg | Asp | Ser | Leu | Thr | Phe | Gly | Asn | Phe | Asn | |
| | | 150 | | | | | 155 | | | | | 160 | | | | |

| | | | | | | | | | | | | | | | | |
|---|---|---|---|---|---|---|---|---|---|---|---|---|---|---|---|---|
| AAG | TAC | CTG | TAT | GCC | TCC | GAG | GGG | GGT | GAG | GGC | GTT | GAC | GCC | TAC | ACC | 994 |
| Lys | Tyr | Leu | Tyr | Ala | Ser | Glu | Gly | Gly | Glu | Gly | Val | Asp | Ala | Tyr | Thr | |
| 165 | | | | | 170 | | | | | 175 | | | | | | |

| | | | | | | | | | | | | | | | | |
|---|---|---|---|---|---|---|---|---|---|---|---|---|---|---|---|---|
| ATT | GAC | ACG | GGT | ATC | AAC | GTT | GAC | CAC | GTT | GAC | TTC | GAG | GGC | CGT | GCC | 1042 |
| Ile | Asp | Thr | Gly | Ile | Asn | Val | Asp | His | Val | Asp | Phe | Glu | Gly | Arg | Ala | |
| 180 | | | | | 185 | | | | | 190 | | | | | 195 | |

| | | | | | | | | | | | | | | | | |
|---|---|---|---|---|---|---|---|---|---|---|---|---|---|---|---|---|
| ACT | TGG | GGC | AAG | ACA | ATC | CCT | ACC | AAC | GAT | GAA | GAT | CTC | GAT | GGC | AAT | 1090 |
| Thr | Trp | Gly | Lys | Thr | Ile | Pro | Thr | Asn | Asp | Glu | Asp | Leu | Asp | Gly | Asn | |
| | | | | 200 | | | | | 205 | | | | | 210 | | |

| | | | | | | | | | | | | | | | | |
|---|---|---|---|---|---|---|---|---|---|---|---|---|---|---|---|---|
| GGT | CAC | GGA | ACT | CAC | TGC | TCC | GGA | ACC | ATG | GCT | GGT | AAG | AAG | TAC | GGT | 1138 |
| Gly | His | Gly | Thr | His | Cys | Ser | Gly | Thr | Met | Ala | Gly | Lys | Lys | Tyr | Gly | |
| | | | | 215 | | | | | 220 | | | | | 225 | | |

| | | | | | | | | | | | | | | | | |
|---|---|---|---|---|---|---|---|---|---|---|---|---|---|---|---|---|
| GTT | GCC | AAG | AAG | GCC | AAC | CTC | TAT | GCT | GTC | AAG | GTC | CTC | CGG | TCG | AGC | 1186 |
| Val | Ala | Lys | Lys | Ala | Asn | Leu | Tyr | Ala | Val | Lys | Val | Leu | Arg | Ser | Ser | |
| | | 230 | | | | | 235 | | | | | 240 | | | | |

| | | | | | | | | | | | | | | | | |
|---|---|---|---|---|---|---|---|---|---|---|---|---|---|---|---|---|
| GGC | TCT | GGC | ACC | ATG | TCT | GAT | GTC | GTT | TCT | GGT | GTC | GAG | TAT | GCC | GTC | 1234 |
| Gly | Ser | Gly | Thr | Met | Ser | Asp | Val | Val | Ser | Gly | Val | Glu | Tyr | Ala | Val | |
| 245 | | | | | 250 | | | | | 255 | | | | | | |

| | | | | | | | | | | | | | | | | |
|---|---|---|---|---|---|---|---|---|---|---|---|---|---|---|---|---|
| CAG | GCT | CAT | ATC | AAG | AAG | GCC | AAG | GAT | GCC | AAG | AAC | GGC | AAG | GTC | AAG | 1282 |
| Gln | Ala | His | Ile | Lys | Lys | Ala | Lys | Asp | Ala | Lys | Asn | Gly | Lys | Val | Lys | |
| 260 | | | | | 265 | | | | | 270 | | | | | 275 | |

| | | | | | | | | | | | | | | | | |
|---|---|---|---|---|---|---|---|---|---|---|---|---|---|---|---|---|
| GGA | TTC | AAG | GGC | AGC | GTT | GCC | AAC | ATG | AGT | CTC | GGT | GGT | GGC | AAG | TCT | 1330 |
| Gly | Phe | Lys | Gly | Ser | Val | Ala | Asn | Met | Ser | Leu | Gly | Gly | Gly | Lys | Ser | |
| | | | | 280 | | | | | 285 | | | | | 290 | | |

| | | | | | | | | | | | | | | | | |
|---|---|---|---|---|---|---|---|---|---|---|---|---|---|---|---|---|
| AAG | ACC | CTC | GAG | GAT | GCT | GTT | AAC | GCT | GGT | GTT | GAG | GCT | GGT | CTT | CAC | 1378 |
| Lys | Thr | Leu | Glu | Asp | Ala | Val | Asn | Ala | Gly | Val | Glu | Ala | Gly | Leu | His | |
| | | | | 295 | | | | | 300 | | | | | 305 | | |

| | | | | | | | | | | | | | | | | |
|---|---|---|---|---|---|---|---|---|---|---|---|---|---|---|---|---|
| TTC | GCC | GTT | GCC | GCC | GGT | AAT | GAC | AAT | GCT | GAT | GCT | TGC | AAC | TAC | TCT | 1426 |
| Phe | Ala | Val | Ala | Ala | Gly | Asn | Asp | Asn | Ala | Asp | Ala | Cys | Asn | Tyr | Ser | |
| | | | 310 | | | | | 315 | | | | | 320 | | | |

| | | | | | | | | | | | | | | | | |
|---|---|---|---|---|---|---|---|---|---|---|---|---|---|---|---|---|
| CCT | GCT | GCT | GCC | GAG | AAG | GCC | ATC | ACC | GTT | GGT | GCC | TCG | ACA | CTT | GCT | 1474 |
| Pro | Ala | Ala | Ala | Glu | Lys | Ala | Ile | Thr | Val | Gly | Ala | Ser | Thr | Leu | Ala | |
| | | 325 | | | | | 330 | | | | | 335 | | | | |

| | | | | | | | | | | | | | | | | |
|---|---|---|---|---|---|---|---|---|---|---|---|---|---|---|---|---|
| GAC | GAG | CGT | GCG | TAC | TTC | TCC | AAC | TAC | GGA | GAG | TGC | ACT | GAC | ATC | TTC | 1522 |
| Asp | Glu | Arg | Ala | Tyr | Phe | Ser | Asn | Tyr | Gly | Glu | Cys | Thr | Asp | Ile | Phe | |
| 340 | | | | | 345 | | | | | 350 | | | | | 355 | |

| | | | | | | | | | | | | | | | | |
|---|---|---|---|---|---|---|---|---|---|---|---|---|---|---|---|---|
| GCT | CCT | GGT | CTC | AAC | ATC | CTG | TCC | ACC | TGG | ATT | GGC | AGC | AAC | TAC | GCC | 1570 |
| Ala | Pro | Gly | Leu | Asn | Ile | Leu | Ser | Thr | Trp | Ile | Gly | Ser | Asn | Tyr | Ala | |
| | | | | 360 | | | | | 365 | | | | | 370 | | |

| | | | | | | | | | | | | | | | | |
|---|---|---|---|---|---|---|---|---|---|---|---|---|---|---|---|---|
| ACC | AAC | ATC | ATC | TCT | GGC | ACT | TCC | ATG | GCC | TCT | CCT | CAC | ATT | GCT | GGC | 1618 |
| Thr | Asn | Ile | Ile | Ser | Gly | Thr | Ser | Met | Ala | Ser | Pro | His | Ile | Ala | Gly | |
| | | | 375 | | | | | 380 | | | | | 385 | | | |

| | | | | | | | | | | | | | | | | |
|---|---|---|---|---|---|---|---|---|---|---|---|---|---|---|---|---|
| CTG | CTG | GCC | TAC | TTT | GTC | TCC | CTC | CAG | CCC | TCC | TCG | GAC | TCT | GCA | TTC | 1666 |
| Leu | Leu | Ala | Tyr | Phe | Val | Ser | Leu | Gln | Pro | Ser | Ser | Asp | Ser | Ala | Phe | |
| | | | 390 | | | | | 395 | | | | | 400 | | | |

| | | | | | | | | | | | | | | | | |
|---|---|---|---|---|---|---|---|---|---|---|---|---|---|---|---|---|
| GCT | GTT | GAG | GAG | CTT | ACT | CCT | GCT | AAG | CTG | AAG | AAG | GAC | ATC | ATC | GCC | 1714 |

|  |  |  |  |  |  |  |  |  |  |  |  |  |  |  |
|---|---|---|---|---|---|---|---|---|---|---|---|---|---|---|
| Ala | Val | Glu | Glu | Leu | Thr | Pro | Ala | Lys | Leu | Lys | Lys | Asp | Ile | Ile | Ala |
|  | 405 |  |  |  | 410 |  |  |  | 415 |  |  |  |  |  |

| ATC | GCC | ACC | GAG | GGC | GCT | CTC | ACT | GAC | ATT | CCC | TCC | AAC | ACC | CCC | AAC | 1762 |
|---|---|---|---|---|---|---|---|---|---|---|---|---|---|---|---|---|
| Ile | Ala | Thr | Glu | Gly | Ala | Leu | Thr | Asp | Ile | Pro | Ser | Asn | Thr | Pro | Asn |  |
| 420 |  |  |  |  | 425 |  |  |  | 430 |  |  |  |  | 435 |  |  |

| GTA | AGT | CAT | GCC | GCT | GTT | GGT | ATT | TAT | AAG | AGA | AAC | GAG | CTA | ACT | CAG | 1810 |
|---|---|---|---|---|---|---|---|---|---|---|---|---|---|---|---|---|
| Val | Ser | His | Ala | Ala | Val | Gly | Ile | Tyr | Lys | Arg | Asn | Glu | Leu | Thr | Gln |  |
|  |  |  |  | 440 |  |  |  |  | 445 |  |  |  |  | 450 |  |  |

| AAA | TTC | AGC | TCC | TTG | CCT | GGA | ACG | GTG | GTG | GTT | CCG | AGA | ACT | ACA | CCG | 1858 |
|---|---|---|---|---|---|---|---|---|---|---|---|---|---|---|---|---|
| Lys | Phe | Ser | Ser | Leu | Pro | Gly | Thr | Val | Val | Val | Pro | Arg | Thr | Thr | Pro |  |
|  |  |  | 455 |  |  |  |  | 460 |  |  |  |  | 465 |  |  |  |

| ACA | TCG | TTG | GCA | GCG | GTG | GCT | ACA | AGG | TCT | CCT | CTG | CCA | AGA | ACC | GCA | 1906 |
|---|---|---|---|---|---|---|---|---|---|---|---|---|---|---|---|---|
| Thr | Ser | Leu | Ala | Ala | Val | Ala | Thr | Arg | Ser | Pro | Leu | Pro | Arg | Thr | Ala |  |
|  |  | 470 |  |  |  |  | 475 |  |  |  |  | 480 |  |  |  |  |

| TCG | AGG | ACC | GTA | TTG | AGG | GTC | TCG | TTC | ACA | AGG | CCG | AAG | AGC | TGC | TCA | 1954 |
|---|---|---|---|---|---|---|---|---|---|---|---|---|---|---|---|---|
| Ser | Arg | Thr | Val | Leu | Arg | Val | Ser | Phe | Thr | Arg | Pro | Lys | Ser | Cys | Ser |  |
|  | 485 |  |  |  |  | 490 |  |  |  |  | 495 |  |  |  |  |  |

| CCG | AGG | AGC | TTG | GTG | CCA | TCT | ACA | GCG | AGA | TCC | AGG | ATG | CCG | TCG | TCG | 2002 |
|---|---|---|---|---|---|---|---|---|---|---|---|---|---|---|---|---|
| Pro | Arg | Ser | Leu | Val | Pro | Ser | Thr | Ala | Arg | Ser | Arg | Met | Pro | Ser | Ser |  |
| 500 |  |  |  |  | 505 |  |  |  |  | 510 |  |  |  |  | 515 |  |

| CAT | AGA | TCA | GAA | CTC | GTG | CTT | TCC | AGA | CGT | AGA | TCG | GAA | GAC | TTG | GTT | 2050 |
|---|---|---|---|---|---|---|---|---|---|---|---|---|---|---|---|---|
| His | Arg | Ser | Glu | Leu | Val | Leu | Ser | Arg | Arg | Arg | Ser | Glu | Asp | Leu | Val |  |
|  |  |  |  | 520 |  |  |  |  | 525 |  |  |  |  | 530 |  |  |

| TTT | TTT | TGAGGTATGG | GATGGTTGAT | CGGACATTTT | GGCGCTGGTC | TCTTTTTATT | 2106 |
|---|---|---|---|---|---|---|---|
| Phe | Phe |  |  |  |  |  |  |

| GTGTTTGGTC | TCGAAGACGC | TGATGCATTG | ACTGTATCGG | CTGTATCACT | CCGCCCCTGC | 2166 |
|---|---|---|---|---|---|---|
| TTATCTGTTT | GGTTCATCTT | TATGGTAGTA | TACATGTCTG | CAAAGAAGGT | TTTGTTACCT | 2226 |
| CACTTAGAAT | GTTCTGGTTC | TATAACAGAC | TGACAATCTC | ACTGGGTTAT | CTAAGAGATC | 2286 |
| TGACAAACGC | TTGGTAGAAG | AGAAAGGTGA | GGGAGTAGAC | ATCATCAGTC | TAAATCCACA | 2346 |
| TTACGACATG | CCGTAATAGA | TGAGAGCACC | GGATGCTAGC | CTTTGTAGAC | TACAAAGGAG | 2406 |
| AAAACCCCTA | GGAAAGGTAA | TTTCTAAGTC | ATGCCCACCT | ATTCTCTCTA | TCTCTTACTG | 2466 |
| AGACAGTCAA | TCCCATGACG | AACAACTAAT | GACATCATGG | GTCACGCTAC | GGGGTCATGC | 2526 |
| CGAAACGAAG | CCGAAGTACT | ACTCCTAAGT | AAAGCCACAA | CTTTGCATAC | GTTCATTCAG | 2586 |
| GAAACGGAAA | CACAGGAGGA | AGAATATTGA | AATATCTTGA | GGGGCTTCAT | ATAGAATAGA | 2646 |
| CAGATATATA | ATAGTTGTCA | AAGTATACAA | AAAGACCTCA | TGCATGCTAA | CAGATAAAGC | 2706 |
| AAAGGATCTC | ATATTGATAG | ACTGTGCTGT | ATACCACCTC | TTAATGCAGC | GCCTGCGCTA | 2766 |
| TGCCACGATG | AAATATAAAG | GGGGAAAAAG | TCATGTAAGT | AGTAAGTAGA | AACTCCAAGC | 2826 |
| GCCAAATATA | TAGATAGTAA | TAGGGGTGGC | GACATAATTT | GGCTTTTATA | CTTGATAGGT | 2886 |
| TGAACAAATC | AAGTGGCCCT | GTGCTCGTCT | TCCTCCTCAT | CACTGCCGGA | ATCTTGGTCT | 2946 |
| TCGTCATCGT | CATCGACGTC | AAGGTCCTCG | TCGGAGTCGC | TACCGCCGAA | GACGTCGTCG | 3006 |
| TCCACATCGC | TCTCGGCCCA | GAAGTCGGAG | TCGTCCTTCT | CCACAGGTTT | GGAGACTGTC | 3066 |
| GTGGTGGATT | CGTGAGTCGG | CATGACGAAT | CCCTCGGGAA | TATCGTTCTT | CGAATCCTCC | 3126 |
| ACGTGCTGTT | TCACGATCGA | TTTGTATTCG | TCGGGCTCT  | TGCGCAACAT | GACCGAGGCG | 3186 |
| TCAACGTTGG | CGGGGGAAGA | GATCCGGGGA | ATTC |  |  | 3220 |

( 2 ) INFORMATION FOR SEQ ID NO:2:

( i ) SEQUENCE CHARACTERISTICS:
        ( A ) LENGTH: 533 amino acids
        ( B ) TYPE: amino acid
        ( D ) TOPOLOGY: linear (i i) MOLECULE TYPE: protein (x i) SEQUENCE DESCRIPTION: SEQ ID NO:2:

```
Met  Lys  Gly  Ile  Leu  Gly  Leu  Ser  Leu  Leu  Pro  Leu  Leu  Thr  Ala  Ala
 1              5                        10                       15
Ser  Pro  Val  Phe  Val  Asp  Ser  Ile  His  Asn  Glu  Ala  Ala  Pro  Ile  Leu
               20                        25                       30
Ser  Ala  Thr  Asn  Ala  Lys  Glu  Val  Pro  Asp  Ser  Tyr  Ile  Val  Val  Phe
          35                        40                       45
Lys  Lys  His  Val  Thr  Ser  Glu  Leu  Ala  Ser  Ala  His  His  Ser  Trp  Val
     50                        55                       60
Gln  Asp  Ile  His  Asp  Ser  Gln  Ser  Glu  Arg  Thr  Glu  Leu  Lys  Lys  Arg
 65                      70                       75                       80
Ser  Leu  Phe  Gly  Leu  Gly  Asp  Glu  Val  Tyr  Leu  Gly  Leu  Lys  Asn  Thr
                    85                       90                       95
Phe  Asp  Ile  Ala  Gly  Ser  Leu  Ile  Gly  Tyr  Ser  Gly  His  Phe  His  Glu
               100                       105                      110
Asp  Val  Ile  Glu  Gln  Val  Arg  Arg  His  Pro  Asp  Val  Asp  Tyr  Ile  Glu
               115                       120                      125
Arg  Asp  Ser  Glu  Val  His  Thr  Met  Glu  Gly  Ala  Thr  Glu  Lys  Asn  Ala
     130                       135                      140
Pro  Trp  Gly  Leu  Ala  Arg  Ile  Ser  His  Arg  Asp  Ser  Leu  Thr  Phe  Gly
145                       150                      155                      160
Asn  Phe  Asn  Lys  Tyr  Leu  Tyr  Ala  Ser  Glu  Gly  Glu  Gly  Val
                    165                      170                      175   Asp
Ala  Tyr  Thr  Ile  Asp  Thr  Gly  Ile  Asn  Val  Asp  His  Val  Asp  Phe  Glu
               180                       185                      190
Gly  Arg  Ala  Thr  Trp  Gly  Lys  Thr  Ile  Pro  Thr  Asn  Asp  Glu  Asp  Leu
          195                       200                      205
Asp  Gly  Asn  Gly  His  Gly  Thr  His  Cys  Ser  Gly  Thr  Met  Ala  Gly  Lys
     210                       215                      220
Lys  Tyr  Gly  Val  Ala  Lys  Lys  Ala  Asn  Leu  Tyr  Ala  Val  Lys  Val  Leu
225                       230                      235                      240
Arg  Ser  Ser  Gly  Ser  Gly  Thr  Met  Ser  Asp  Val  Val  Ser  Gly  Val  Glu
                    245                      250                      255
Tyr  Ala  Val  Gln  Ala  His  Ile  Lys  Lys  Ala  Lys  Asp  Ala  Lys  Asn  Gly
               260                       265                      270
Lys  Val  Lys  Gly  Phe  Lys  Gly  Ser  Val  Ala  Asn  Met  Ser  Leu  Gly  Gly
          275                       280                      285
Gly  Lys  Ser  Lys  Thr  Leu  Glu  Asp  Ala  Val  Asn  Ala  Gly  Val  Glu  Ala
     290                       295                      300
Gly  Leu  His  Phe  Ala  Val  Ala  Ala  Gly  Asn  Asp  Asn  Ala  Asp  Ala  Cys
305                       310                      315                      320
Asn  Tyr  Ser  Pro  Ala  Ala  Ala  Glu  Lys  Ala  Ile  Thr  Val  Gly  Ala  Ser
                    325                      330                      335
Thr  Leu  Ala  Asp  Glu  Arg  Ala  Tyr  Phe  Ser  Asn  Tyr  Gly  Glu  Cys  Thr
               340                       345                      350
Asp  Ile  Phe  Ala  Pro  Gly  Leu  Asn  Ile  Leu  Ser  Thr  Trp  Ile  Gly  Ser
          355                       360                      365
Asn  Tyr  Ala  Thr  Asn  Ile  Ile  Ser  Gly  Thr  Ser  Met  Ala  Ser  Pro  His
     370                       375                      380
Ile  Ala  Gly  Leu  Leu  Ala  Tyr  Phe  Val  Ser  Leu  Gln  Pro  Ser  Ser  Asp
385                       390                      395                      400
Ser  Ala  Phe  Ala  Val  Glu  Glu  Leu  Thr  Pro  Ala  Lys  Leu  Lys  Lys  Asp
```

|     |     |     |     | 405 |     |     |     |     | 410 |     |     |     |     | 415 |     |     |
| --- | --- | --- | --- | --- | --- | --- | --- | --- | --- | --- | --- | --- | --- | --- | --- | --- |
| Ile | Ile | Ala | Ile | Ala | Thr | Glu | Gly | Ala | Leu | Thr | Asp | Ile | Pro | Ser | Asn |
|     |     |     | 420 |     |     |     |     | 425 |     |     |     |     | 430 |     |     |
| Thr | Pro | Asn | Val | Ser | His | Ala | Ala | Val | Gly | Ile | Tyr | Lys | Arg | Asn | Glu |
|     |     | 435 |     |     |     |     | 440 |     |     |     |     | 445 |     |     |     |
| Leu | Thr | Gln | Lys | Phe | Ser | Ser | Leu | Pro | Gly | Thr | Val | Val | Val | Pro | Arg |
|     | 450 |     |     |     |     | 455 |     |     |     |     | 460 |     |     |     |     |
| Thr | Thr | Pro | Thr | Ser | Leu | Ala | Ala | Val | Ala | Thr | Arg | Ser | Pro | Leu | Pro |
| 465 |     |     |     |     | 470 |     |     |     |     | 475 |     |     |     |     | 480 |
| Arg | Thr | Ala | Ser | Arg | Thr | Val | Leu | Arg | Val | Ser | Phe | Thr | Arg | Pro | Lys |
|     |     |     |     | 485 |     |     |     |     | 490 |     |     |     |     | 495 |     |
| Ser | Cys | Ser | Pro | Arg | Ser | Leu | Val | Pro | Ser | Thr | Ala | Arg | Ser | Arg | Met |
|     |     |     | 500 |     |     |     |     | 505 |     |     |     |     | 510 |     |     |
| Pro | Ser | Ser | His | Arg | Ser | Glu | Leu | Val | Leu | Ser | Arg | Arg | Arg | Ser | Glu |
|     |     | 515 |     |     |     |     | 520 |     |     |     |     | 525 |     |     |     |
| Asp | Leu | Val | Phe | Phe |
|     |     | 530 |     |     |

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 1..19
        ( D ) OTHER INFORMATION: /note= "region homologous to A. niger pepC"

( i x ) FEATURE:
        ( A ) NAME/KEY: misc_feature
        ( B ) LOCATION: 20..37
        ( D ) OTHER INFORMATION: /note= "region homologous to A. niger pki gene"

( x i ) SEQUENCE DESCRIPTION: SEQ ID NO:3:

GGCCGAGGAT GCCCTTCATC TTGACGGATG ATTGATC           37

( 2 ) INFORMATION FOR SEQ ID NO:4:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCCGAGGATG CCCTTCATCT TGAATTCGGA TGATTGATCT CTAC           44

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

```
GCTCGATGTA ATCGACATCG GGGTGTCTGC GG                                              32
```

( 2 ) INFORMATION FOR SEQ ID NO:6:

( i ) SEQUENCE CHARACTERISTICS:
        ( A ) LENGTH: 2993 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Aspergillus niger
        ( B ) STRAIN: N400

( v i i ) IMMEDIATE SOURCE:
        ( B ) CLONE: pTZPEPD ( i x ) FEATURE:
        ( A ) NAME/KEY: promoter
        ( B ) LOCATION: 1..829

( i x ) FEATURE:
        ( A ) NAME/KEY: CDS
        ( B ) LOCATION: join(830..1153, 1205..1649, 1697..1785, 1841
            . . 2233)
        ( D ) OTHER INFORMATION: /note= "subtilisin-type protease
        PEPD of Aspergillus niger; product of gene pepD"

( i x ) FEATURE:
        ( A ) NAME/KEY: intron
        ( B ) LOCATION: 1154..1204

( i x ) FEATURE:
        ( A ) NAME/KEY: intron
        ( B ) LOCATION: 1650..1696

( i x ) FEATURE:
        ( A ) NAME/KEY: intron
        ( B ) LOCATION: 1786..1840

( x i ) SEQUENCE DESCRIPTION: SEQ ID NO:6:

```
AAGCTTCGTA TATAATTCCC TTTTGACAAT GTCAAAATCT TTTGGACCAC TAATATAGCT              60
GCATGGACCG GTTAATCAGA GGTTATTTTT GTGCTCGAAT GCCGTGTAAC ATTGGATAAT             120
AGTACACTCC TTTCACCCAC CCTCAGATGC CCGCCCCCTA CAGTAGGGTT GTCAATATCC             180
CTCACCTTTC CAATTGCTGA TGCAGAATGG ACCTGATATA GAAGCCTCAC AGCACCAGAG             240
ACTACCGCCT GAAGATGCCA AGTATTGATG GGTTACATTG CTGGCGAAT  AGACTGTTCA             300
CCATCCCCCG CCTGTACAAG GCTCATTGAG CGACCTTTAT TTCTATGAAG GCTTCTTGCA             360
GTGTAGAGCC GCTGTTTAGA ACTCGGAAAT AGGCGTGCAT AGTATGAACT CAATCAGCAG             420
AGTCAATCGA TTGACACTAA CGCCTAGCAA GCAATCAGTG CTCAGAGGAA GCTAACAGAT             480
GGCTGGTTAA GCTGCCCCAG AAACGAAATG TGTCCGCAAT CCCATCCCTG CATGCTTATC             540
TGTATTCTGT GCATGCATGA TGCTTTCCTC ACGGGGCATT ACCCAGTAGT CCGAAGACGC             600
AATGTGACCA TCTGACTGAG TTTTAAATAT ACTGTCCAAG TGCCTTCTGA CCCGGTCCCC             660
```

```
GCTTGATGAC  AATCAACAAA  AGGTGAATGT  GACTGAAAGG  CGTGGTCCAG  ACAACAGGCC      720

TTAGACTTTA  TTGTGAGACT  ATAAAGGAT   CTAACTATTG  CACTACTGAA  ATTAAGCATT      780

CTAGTCTACC  ATTGACATTT  CTCCCCTTTC  GGTGGGCCAC  TCGCTCAAC   ATG GCT         835
                                                            Met Ala
                                                             1
```

```
TTC CTC AAA CGC ATT CTC CCG CTG CTG GCC CTC ATC TTG CCT GCA GTT             883
Phe Leu Lys Arg Ile Leu Pro Leu Leu Ala Leu Ile Leu Pro Ala Val
         5                   10                  15

TTC AGT GCC ACA GAA CAG GTC CCT CAT CCG ACC ATC CAG ACC ATC CCG             931
Phe Ser Ala Thr Glu Gln Val Pro His Pro Thr Ile Gln Thr Ile Pro
        20              25                  30

GGG AAG TAC ATT GTT ACT TTC AAG TCC GGC ATT GAC AAT GCG AAA ATT             979
Gly Lys Tyr Ile Val Thr Phe Lys Ser Gly Ile Asp Asn Ala Lys Ile
 35              40                  45                      50

GAG TCT CAT GCC GCA TGG GTA ACG GAG CTC CAC AGG CGC AGC TTA GAA            1027
Glu Ser His Ala Ala Trp Val Thr Glu Leu His Arg Arg Ser Leu Glu
                 55                  60                  65

GGC CGC AGT ACA ACC GAA GAT GAC CTT CCC GCC GGG ATC GAG AGA ACT            1075
Gly Arg Ser Thr Thr Glu Asp Asp Leu Pro Ala Gly Ile Glu Arg Thr
             70                  75                  80

TAC AGA ATT GCC AAT TTT GCT GGG TAC GCG GGG TCT TTC GAT GAG AAA            1123
Tyr Arg Ile Ala Asn Phe Ala Gly Tyr Ala Gly Ser Phe Asp Glu Lys
         85                  90                  95

ACT ATC GAG GAG ATC CGC AAA CAT AAC CAT GTTTGTGTCC ACGTATCCCA              1173
Thr Ile Glu Glu Ile Arg Lys His Asn His
100                 105

GGCCGTATGG TTTCGACTAA CTGCTGTACA G GTA GCC TAT GTG GAA CAA GAT             1225
                                  Val Ala Tyr Val Glu Gln Asp
                                      110                 115

CAG GTC TGG TAC CTC GAT ACG CTA GTT ACC GAA AGA CGA GCT CCT TGG            1273
Gln Val Trp Tyr Leu Asp Thr Leu Val Thr Glu Arg Arg Ala Pro Trp
                 120                 125                 130

GGA CTG GGG AGC ATC TCT CAC CGT GGT GCG TCT AGC ACC GAC TAC ATC            1321
Gly Leu Gly Ser Ile Ser His Arg Gly Ala Ser Ser Thr Asp Tyr Ile
             135                 140                 145

TAT GAT GAC AGC GCT GGG GAG GGT ACA TAC GCT TAT GTA GTG GAC ACT            1369
Tyr Asp Asp Ser Ala Gly Glu Gly Thr Tyr Ala Tyr Val Val Asp Thr
         150                 155                 160

GGC ATC TTG GCT ACG CAT AAT GAG TTT GGT GGT CGT GCT AGC CTG GCA            1417
Gly Ile Leu Ala Thr His Asn Glu Phe Gly Gly Arg Ala Ser Leu Ala
165                 170                 175

TAC AAT GCT GCA GGG GGT GAG CAC GTT GAT GGT GTT GGA CAT GGC ACA            1465
Tyr Asn Ala Ala Gly Gly Glu His Val Asp Gly Val Gly His Gly Thr
180                 185                 190                 195

CAT GTA GCA GGG ACC ATC GGT GGC AAA ACA TAC GGG GTT TCG AAA AAT            1513
His Val Ala Gly Thr Ile Gly Gly Lys Thr Tyr Gly Val Ser Lys Asn
                 200                 205                 210

GCT CAC CTA CTG TCC GTG AAG GTG TTT GTA GGT GAA TCC AGC TCG ACA            1561
Ala His Leu Leu Ser Val Lys Val Phe Val Gly Glu Ser Ser Ser Thr
             215                 220                 225

TCG GTC ATT CTG GAT GGC TTC AAT TGG GCT GCC AAT GAT ATC GTG AGC            1609
Ser Val Ile Leu Asp Gly Phe Asn Trp Ala Ala Asn Asp Ile Val Ser
         230                 235                 240

AAG AAC CGG ACC AGT AAG GCG GCG ATT AAC ATG AGT CTT   G GTATGTGCGC         1659
Lys Asn Arg Thr Ser Lys Ala Ala Ile Asn Met Ser Leu
245                 250                 255

CCTCTCTGGG GATCTAATGC CGTTAACCGT GATGCAG   GT GGA GGC TAC TCC TAT          1713
                                              Gly Gly Gly Tyr Ser Tyr
                                                              260
```

```
GCG  TTT  AAC  AAT  GCA  GTT  GAG  AAT  GCT  TTT  GAC  GAG  GGT  GTG  CTC  TCT       1761
Ala  Phe  Asn  Asn  Ala  Val  Glu  Asn  Ala  Phe  Asp  Glu  Gly  Val  Leu  Ser
          265                     270                     275

TGT  GTT  GCC  GCT  GGA  AAT  GAG  AAT  GTAAGCTCTG  CTGAACTGTC  CACCATTGAG            1815
Cys  Val  Ala  Ala  Gly  Asn  Glu  Asn
     280                     285

CTAAATTTAG  ACTAATGTTT  TGCAG  AGA  GAT  GCA  GCA  CGG  ACT  AGC  CCG  GCT            1867
                              Arg  Asp  Ala  Ala  Arg  Thr  Ser  Pro  Ala
                                             290                     295

TCT  GCA  CCC  GAC  GCC  ATT  ACT  GTT  GCC  GCT  ATC  AAC  AGA  AGC  AAT  GCC       1915
Ser  Ala  Pro  Asp  Ala  Ile  Thr  Val  Ala  Ala  Ile  Asn  Arg  Ser  Asn  Ala
                    300                     305                     310

CGT  GCG  TCA  TTC  TCA  AAC  TAC  GGC  TCT  GTG  GTT  GAC  ATT  TTT  GCC  CCG       1963
Arg  Ala  Ser  Phe  Ser  Asn  Tyr  Gly  Ser  Val  Val  Asp  Ile  Phe  Ala  Pro
               315                     320                     325

GGA  GAG  CAA  GTA  CTT  TCT  GCA  TGG  ACC  GGC  TCG  AAC  TCG  GCC  ACC  AAC       2011
Gly  Glu  Gln  Val  Leu  Ser  Ala  Trp  Thr  Gly  Ser  Asn  Ser  Ala  Thr  Asn
          330                     335                     340

ACG  ATC  TCC  GGC  ACG  TCC  ATG  GCT  ACA  CCT  CAT  GTG  ACA  GGT  TTG  ATC       2059
Thr  Ile  Ser  Gly  Thr  Ser  Met  Ala  Thr  Pro  His  Val  Thr  Gly  Leu  Ile
          345                     350                     355

CTC  TAT  TTG  ATG  GGC  TTG  CGG  GAC  CTT  GCT  ACC  CCA  GCG  GCT  GCA  ACG       2107
Leu  Tyr  Leu  Met  Gly  Leu  Arg  Asp  Leu  Ala  Thr  Pro  Ala  Ala  Ala  Thr
360                      365                     370                     375

ACC  GAG  CTC  AAG  AGG  TTG  GCT  ACG  CGG  AAT  GCT  GTC  ACC  AAT  GTG  GCG       2155
Thr  Glu  Leu  Lys  Arg  Leu  Ala  Thr  Arg  Asn  Ala  Val  Thr  Asn  Val  Ala
                    380                     385                     390

GGT  AGC  CCC  AAT  CTT  CTG  GCC  TAC  AAT  GGA  AAC  AGC  GGC  GTG  TCA  AAA       2203
Gly  Ser  Pro  Asn  Leu  Leu  Ala  Tyr  Asn  Gly  Asn  Ser  Gly  Val  Ser  Lys
               395                     400                     405

GGG  GGT  AGC  GAT  GAT  GGA  GAT  GAG  GAC  TAGGTGCGTA  ACATGAGTGA                   2250
Gly  Gly  Ser  Asp  Asp  Gly  Asp  Glu  Asp
          410                     415

ATATGGCTTA  GAATAGTGGG  GATCGGAGAG  TAGACTAGTT  TATATGCGAA  ATAAAGTGTG               2310

TATCAGCACC  CTGGCCTGTT  CATGTAAGTC  GGCATTTTCA  CTTTTGCCGA  CACCGCAAAT               2370

ATGCTGTGCT  TGAGGCTGTT  GCCTCCCCAG  CCAGCCTTCC  CGAGACTGAA  ACTCACACAT               2430

CCATTGGATG  TATAAAGTTC  TGCACATGCG  AAATGCCGCT  GCCGCTTACC  TCCCGACGTG               2490

GTACCGGACC  GAAGGCAGAC  ACAGATCATG  GACCGCTATA  CCGCACAGAC  AACTTGTGCT               2550

CCTTACTGAA  AGTACCATTC  CACAGGTCAT  TGCAGCATGA  TGAGTGATGA  TGTACTTCTC               2610

CCCATCAAGA  ACCACTGACG  GTGGTTGGAA  TGAATCTAGA  TCAAAGAGAT  CAACCGCTTC               2670

CCCAGACAGA  TCAGGCCTAT  GCCCATAATG  AACCGGTGAC  TGTGTAACCC  TGTTACAATC               2730

CGTTTGTTAT  TGGTCCTTTC  TGTTTGCTGG  ATGGCGTGTA  CTACCTCAGA  GCTTGTGCTC               2790

CTAGGAGCTC  ATACTGGAGA  CAGGTTCTTG  TATATAGTCA  TAGCCTAAGT  CCGGTGTCTA               2850

GGAAACAGTA  TGCTCGAGGT  CTTTTCCGAT  TCTCACAATG  AGAACTGTCG  CCCGGGTCTT               2910

TACGGCCCCT  GTGGAAAGCG  AAAAGGAGAC  GCTTCTGGCG  CTGCTTCCGC  AATACGGGCT               2970

CAAACTAGCC  CCGGACGGGA  TCC                                                          2993
```

( 2 ) INFORMATION FOR SEQ ID NO:7:

( i ) SEQUENCE CHARACTERISTICS:
        ( A ) LENGTH: 416 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| Met | Ala | Phe | Leu | Lys | Arg | Ile | Leu | Pro | Leu | Leu | Ala | Leu | Ile | Leu | Pro |
|---|---|---|---|---|---|---|---|---|---|---|---|---|---|---|---|
| 1 | | | | 5 | | | | | 10 | | | | | 15 | |
| Ala | Val | Phe | Ser | Ala | Thr | Glu | Gln | Val | Pro | His | Pro | Thr | Ile | Gln | Thr |
| | | | 20 | | | | | 25 | | | | | 30 | | |
| Ile | Pro | Gly | Lys | Tyr | Ile | Val | Thr | Phe | Lys | Ser | Gly | Ile | Asp | Asn | Ala |
| | | 35 | | | | | 40 | | | | | 45 | | | |
| Lys | Ile | Glu | Ser | His | Ala | Ala | Trp | Val | Thr | Glu | Leu | His | Arg | Arg | Ser |
| | 50 | | | | | 55 | | | | | 60 | | | | |
| Leu | Glu | Gly | Arg | Ser | Thr | Thr | Glu | Asp | Asp | Leu | Pro | Ala | Gly | Ile | Glu |
| 65 | | | | | 70 | | | | | 75 | | | | | 80 |
| Arg | Thr | Tyr | Arg | Ile | Ala | Asn | Phe | Ala | Gly | Tyr | Ala | Gly | Ser | Phe | Asp |
| | | | | 85 | | | | | 90 | | | | | 95 | |
| Glu | Lys | Thr | Ile | Glu | Glu | Ile | Arg | Lys | His | Asn | His | Val | Ala | Tyr | Val |
| | | | 100 | | | | | 105 | | | | | 110 | | |
| Glu | Gln | Asp | Gln | Val | Trp | Tyr | Leu | Asp | Thr | Leu | Val | Thr | Glu | Arg | Arg |
| | | 115 | | | | | 120 | | | | | 125 | | | |
| Ala | Pro | Trp | Gly | Leu | Gly | Ser | Ile | Ser | His | Arg | Gly | Ala | Ser | Ser | Thr |
| | 130 | | | | | 135 | | | | | 140 | | | | |
| Asp | Tyr | Ile | Tyr | Asp | Asp | Ser | Ala | Gly | Glu | Gly | Thr | Tyr | Ala | Tyr | Val |
| 145 | | | | | 150 | | | | | 155 | | | | | 160 |
| Val | Asp | Thr | Gly | Ile | Leu | Ala | Thr | His | Asn | Glu | Phe | Gly | Gly | Arg | Ala |
| | | | | 165 | | | | | 170 | | | | | 175 | |
| Ser | Leu | Ala | Tyr | Asn | Ala | Ala | Gly | Gly | Glu | His | Val | Asp | Gly | Val | Gly |
| | | | 180 | | | | | 185 | | | | | 190 | | |
| His | Gly | Thr | His | Val | Ala | Gly | Thr | Ile | Gly | Gly | Lys | Thr | Tyr | Gly | Val |
| | | 195 | | | | | 200 | | | | | 205 | | | |
| Ser | Lys | Asn | Ala | His | Leu | Leu | Ser | Val | Lys | Val | Phe | Val | Gly | Glu | Ser |
| | 210 | | | | | 215 | | | | | 220 | | | | |
| Ser | Ser | Thr | Ser | Val | Ile | Leu | Asp | Gly | Phe | Asn | Trp | Ala | Ala | Asn | Asp |
| 225 | | | | | 230 | | | | | 235 | | | | | 240 |
| Ile | Val | Ser | Lys | Asn | Arg | Thr | Ser | Lys | Ala | Ala | Ile | Asn | Met | Ser | Leu |
| | | | | 245 | | | | | 250 | | | | | 255 | |
| Gly | Gly | Gly | Tyr | Ser | Tyr | Ala | Phe | Asn | Asn | Ala | Val | Glu | Asn | Ala | Phe |
| | | | 260 | | | | | 265 | | | | | 270 | | |
| Asp | Glu | Gly | Val | Leu | Ser | Cys | Val | Ala | Ala | Gly | Asn | Glu | Asn | Arg | Asp |
| | | 275 | | | | | 280 | | | | | 285 | | | |
| Ala | Ala | Arg | Thr | Ser | Pro | Ala | Ser | Ala | Pro | Asp | Ala | Ile | Thr | Val | Ala |
| | 290 | | | | | 295 | | | | | 300 | | | | |
| Ala | Ile | Asn | Arg | Ser | Asn | Ala | Arg | Ala | Ser | Phe | Ser | Asn | Tyr | Gly | Ser |
| 305 | | | | | 310 | | | | | 315 | | | | | 320 |
| Val | Val | Asp | Ile | Phe | Ala | Pro | Gly | Glu | Gln | Val | Leu | Ser | Ala | Trp | Thr |
| | | | | 325 | | | | | 330 | | | | | 335 | |
| Gly | Ser | Asn | Ser | Ala | Thr | Asn | Thr | Ile | Ser | Gly | Thr | Ser | Met | Ala | Thr |
| | | | 340 | | | | | 345 | | | | | 350 | | |
| Pro | His | Val | Thr | Gly | Leu | Ile | Leu | Tyr | Leu | Met | Gly | Leu | Arg | Asp | Leu |
| | | 355 | | | | | 360 | | | | | 365 | | | |
| Ala | Thr | Pro | Ala | Ala | Ala | Thr | Thr | Glu | Leu | Lys | Arg | Leu | Ala | Thr | Arg |
| | 370 | | | | | 375 | | | | | 380 | | | | |
| Asn | Ala | Val | Thr | Asn | Val | Ala | Gly | Ser | Pro | Asn | Leu | Leu | Ala | Tyr | Asn |
| 385 | | | | | 390 | | | | | 395 | | | | | 400 |
| Gly | Asn | Ser | Gly | Val | Ser | Lys | Gly | Gly | Ser | Asp | Asp | Gly | Asp | Glu | Asp |
| | | | | 405 | | | | | 410 | | | | | 415 | |

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

GCTGGATCCC AYGGNACNCA YGTNGC      26

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

GCTGGATCCC AYGGNACNCA YTGYGC      26

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

CTAGAATTCG CCATNGANGT NCC      23

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

CTAGAATTCG CCATRCTNGT NCC      23

( 2 ) INFORMATION FOR SEQ ID NO:12:

( i ) SEQUENCE CHARACTERISTICS:

( A ) LENGTH: 17 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

AGAATGGATC CGCGACG                                                                                              17

( 2 ) INFORMATION FOR SEQ ID NO:13:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
                    ( A ) NAME/KEY: misc_feature
                    ( B ) LOCATION: 1..12
                    ( D ) OTHER INFORMATION: /note= "region homologous to A.
                            niger pepD"

( i x ) FEATURE:
                    ( A ) NAME/KEY: misc_feature
                    ( B ) LOCATION: 10..27
                    ( D ) OTHER INFORMATION: /note= "region homologous to A.
                            niger pki gene"

( x i ) SEQUENCE DESCRIPTION: SEQ ID NO:13:

GAGGAAAGCC ATCTTGACGG ATGATTG                                                                                   27

( 2 ) INFORMATION FOR SEQ ID NO:14:

( i ) SEQUENCE CHARACTERISTICS:
                    ( A ) LENGTH: 29 base pairs
                    ( B ) TYPE: nucleic acid
                    ( C ) STRANDEDNESS: single
                    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
                    ( A ) NAME/KEY: misc_feature
                    ( B ) LOCATION: 1..10
                    ( D ) OTHER INFORMATION: /note= "region homologous to A.
                            niger pki gene"

( i x ) FEATURE:
                    ( A ) NAME/KEY: misc_feature
                    ( B ) LOCATION: 8..27
                    ( D ) OTHER INFORMATION: /note= "region homologous to A.
                            niger pepD gene"

( x i ) SEQUENCE DESCRIPTION: SEQ ID NO:14:

CGTCAAGATG GCTTTCCTCA AACGCATTC                                                                                 29

( 2 ) INFORMATION FOR SEQ ID NO:15:

(i) SEQUENCE CHARACTERISTICS:
  (A) LENGTH: 31 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

GGTGGGCCAC GAATTCAACA TGGCTTTCCT C    31

(2) INFORMATION FOR SEQ ID NO:16:

(i) SEQUENCE CHARACTERISTICS:
  (A) LENGTH: 41 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

GGAGATCCGC AAACATAACC ATGTAGCCTA TGTGGAACAA G    41

(2) INFORMATION FOR SEQ ID NO:17:

(i) SEQUENCE CHARACTERISTICS:
  (A) LENGTH: 40 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

GGCGATTAAC ATGAGTCTTG GTGGAGGCTA CTCCTATGCG    40

(2) INFORMATION FOR SEQ ID NO:18:

(i) SEQUENCE CHARACTERISTICS:
  (A) LENGTH: 40 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

GCCGCTGGAA ATGAGAATAG AGATGCAGCA CGGACTAGCC    40

FUNGAL PROTEASE

CROSS REFERENCE TO RELATED APPLICATIONS

This application is a continuation-in-part of U.S. patent application Ser. No. 08/047,214 filed Apr. 13, 1993, now abandoned.

FIELD OF THE INVENTION

The present invention concerns a novel DNA sequence coding for an Aspergillus serine protease of the subtilisin-type, an Aspergillus serine protease of the subtilisin-type per se and a method for the preparation thereof. The invention further concerns a novel Aspergillus mutant strain defective in a serine protein of the subtilisin-type, which is useful for the expression of heterologous protein, and a method for the preparation of such a mutant strain.

BACKGROUND OF THE INVENTION

Aspergillus species, and in particular Aspergillus niger, are used for the industrial production of enzymes used in the food processing industry. A. niger has advantages as a host for the production of recombinant proteins because of its large capacity for secretion of proteins, and because systems are available for its molecular genetic manipulation. However, the presence of proteases in the culture fluid has proven deleterious to the expression of heterologous proteins in A. niger, in fact Aspergilli are used commercially to produce proteases. A number of extracellular proteases from Aspergilli have been described in the literature [Barthomeuf et al., Biotech. Tech. 2:29–34(1988); Barthomeuf et al., Chem. Pharm Bull. (Tokyo) 37:1333–1336(1989); Bosmann, H. B., Biochim. Biophys. Acta 293:476–489 (1973); Ichishima, E., Biochim. Biophys. Acta 258:274–288 (1972); Chopra, S., and Mehta, P., Folia Microbiol. 30:117–125(1985); Krishnan and Vijayalakshimi, J. Chromatogr. 329:165–170(1985)]. The gene pepA encoding aspergillopepsin A from Aspergillus awamori has recently been cloned [Berka et al., Gene 86:153–162(1990)]. The pepA gene product accounts for a major part of the secreted acid proteases of A. niger and strains in which the pepA gene has been deleted have allowed increased expression of heterologous proteins in A. niger var. awamori [Dunn-Coleman et al., Biotechnology 9:976–981(1991)]. Other protease genes have also been recently cloned from Aspergilli and these include an alkaline serine protease of A. oryzae [Tatsumi et al., Mol. Gen. Genet. 219:33–38(1989)], an alkaline serine protease of A. fumigatus [Jaton-Ogay et al., FEMS Microbiol Letts 92:163–168 (1992)], a non-pepsin type acid protease from A. niger var. macrosporus [Inoue et al., J. Biol. Chem. 266:19484–89(1991)] and a metalloprotease called neutral protease II from A. oryzae [Tatsumi et al., Mol. Gen. Genet. 228:97–103(1991)].

Isolated and mutated protease genes of A. niger can be used for gene disruption experiments, i.e. the preparation of mutant strains in which the corresponding natural gene is destroyer. For example, the pepA gene from Aspergillus awamori has been destroyed by gene disruption in order to prepare aspergillopepsin A deficient strains (Berka et al., op. cit.)

However, as mentioned above Aspergilli produce a large number of different proteases and, thus, there is a continuing need for Aspergillus strains deficient in other proteases for the industrial production of proteins. For this purpose there is also a need for other protease genes which can be used for the preparation of protease deficient strains by in vitro mutagenesis, e.g. gene disruption. Moreover, there is also a need for recombinant protease proteins which can be industrially applied for protein processing.

Another major constituent of the secreted protease activities in A. niger are serine proteases [Sakka et al., J. Ferment Technol. 63:479–483(1985)]. Serine proteases from the fungi have been extensively characterised in the mold, T.album, and the yeast Saccharomyces cerevisiae. T. album probably secretes three related serine proteases the best charaterised being proteinase K [Jany et al., FEBS 199:139–144(1986)], while a homologous protein in yeast is localized in the vacuole [Wolf and Ehmann, Eur. J. Biochem. 98:375–384(1979)]. The genes for all of these T.album and S. cerevisiae proteins have been cloned and charactetised [Gunkel and Gassen, Eur. J. Biochem. 179:185–194(1989), Samal et al., Gene 85:329–333(1989), Samal et al., Molec. Microbiol 4:1789–1792(1990), and Moehle et al., Molec. Cell. Biol. 7:4390–99(1987)]. Alkaline serene proteases have also been cloned and characterised in A.oryzae, in A. fumigatus and in Achremonium chrysogenum [Tatsumi et al., Mol. Gen. Genet. 219:33–38 (1989); Jaton-Ogay et al., FEMS Microbiol. Letts. 92:163–168 (1992); Isogai et al., Agric Biol. Chem. 55:471–477 (1991)]

It is now found that Aspergillus also produces serine protean homologous to the subtilisin family of proteases. The present invention focuses on this type of protease.

OBJECT OF THE INVENTION

It is an object of the present invention to provide a DNA molecule encoding an Aspergillus serine protease of the subtilisin type.

A further object is to provide recombinant Aspergillus serine protease of the subtilisin type and for this purpose also a transformed Aspergillus strain for the production thereof.

Another object is to provide an Aspergillus strain defective in a serine protease gene of the subtilisin type which strain can be used for a more efficient production of heterologous proteins.

SUMMARY OF THE INVENTION

The present invention concerns an Aspergillus serine protease of the subtilisin type. Such a protease is herein named "Aspergillus-subtilisin". An "Aspergillus-subtilisin of the present invention is understood as (a) being derived from Aspergillus spec., (b) exhibiting protease activity due to a catalytic serine residue at the active site and (c) having sufficient amino acid sequence homology with known serine proteases for being grouped into the subtilisin family. However, included within the meaning of the term Aspergillus-subtilisin as used in the present invention are also fragments of such an enzyme which retain serine protease activity, however, the full length enzymes arm preferred embodiments. It is understood that also fusion proteins containing an "Aspergillus-subtilisin" of the invention attached to additional amino acids, peptides or proteins are part of the present invention.

In a preferred meaning, Aspergillus-subtilisin describes a protease or active fragment derived from Aspergillus niger, more preferentially a protease or active fragment having the amino acid sequence or part of the sequence shown under SEQ ID NO. 1 and 6, respectively.

The present invention also concerns an isolated DNA sequence encoding an Aspergillus-subtilisin of the present invention, and a hybrid vector for the cloning and multiplication of such a DNA sequence. The invention further concerns an expression hybrid vector for the production of an Aspergillus-subtilisin comprising such a DNA sequence functionally linked with regulatory regions suitable for the expression of an Aspergillus-subtilisin gene in a suitable host cell. The invention also concerns transformed host cells capable of expressing Aspergillus-subtilisin, for example an Aspergillus strain capable of overexpressing Aspergillus-subtilisin due to an increased copy number of the gene after transformation.

The invention also concerns an Aspergillus strain deficient in an Aspergillus-subtilisin gene and a method for the production thereof by means of a DNA sequence encoding Aspergillus-subtilisin which is no longer capable of expressing functional protein due to mutagenesis, e.g. gene disruption.

Moreover, the present invention concerns methods for the preparation of a DNA sequence, hybrid vector, expression vector and Aspergillus-subtilisin of the invention as well as methods for the expression of an Aspergillus strain deficient in an Aspergillus-subtilisin gene and of a host strain overproducing Aspergillus-subtilisin.

DETAILED DESCRIPTION OF THE INVENTION

DNA encoding Aspergillus-subtilisin, hybrid vectors for cloning and expression

The present invention concerns a DNA molecule comprising a DNA sequence encoding an Aspergillus-subtilisin, preferably of *Aspergillus niger*. The DNA sequence may contain one or more introns as have DNA molecules isolatable from a genomic DNA library, e.g. as the pepC gene shown in SEQ ID NO. 1 or the pepD gene shown in SEQ ID NO. 6. However, the invention also concerns an intron-less variant of the DNA sequence, for example, such isolatable by cDNA cloning or after mutagenesis e.g. by applying PCR technology. Such intron-less genes are in particular useful for expression in non-Aspergillus hosts, preferably in procaryotes or yeast.

The invention concerns preferably a DNA molecule comprising a DNA sequence coding for the *A. niger*-subtilisin PEPC having the amino acid sequence shown in SEQ ID NO. 1 or a fragment thereof retaining serine protease activity. A DNA sequence of the invention is preferably the coding region for mature PEPC protease shown in the nucleotide sequence with SEQ ID NO. 1. However, the invention also concerns degenerate DNA sequences coding for PEPC or a fragment thereof, i.e. sequences in which nucleotides are replaced without changing the encoded amino acid sequence. Such DNA sequences are useful, for example, due to differences in the preferred codon usage in different hosts or due to the presence of new recognition sites for restriction enzymes.

Another preferred embodiment of the invention is DNA molecule comprising a DNA sequence coding for the *A. niger*-subtilisin PEPD having the amino acid sequence shown in SEQ ID NO. 6 or a fragment thereof retaining serine protease activity. Another preferred DNA sequence of the invention is thus also the coding region for mature PEPD protease shown in the nucleotide sequence with SEQ ID NO. 6. However, the invention also concerns degenerate DNA sequences coding for PEPD or a fragment thereof, i.e. sequences in which nucleotides are replaced without changing the encoded amino acid sequence.

The invention concerns also a hybrid vector comprising as insert a DNA sequence encoding an Aspergillus-subtilisin of the invention, preferably a preferred form thereof. Such a hybrid vector of the invention is useful for the propagation and multiplication of a DNA sequence of the invention. The invention also concerns an expression vector suitable for the production of an Aspergillus-subtilisin of the invention, preferably of the preferred forms. Such an expression vector comprises an "expression cassette" in which a DNA sequence coding for an Aspergillus-subtilisin is functionally linked with regulatory regions suitable for the control of the expression of such a DNA sequence in a desired host cell.

A hybrid vector of the invention, including an expression vector, may be derived from any vector useful in the art of genetic engineering, such as from viruses, phages, cosmids, plasmids or chromosomal DNA, such as derivatives of SV40, Herpes-viruses, Papilloma viruses, Retroviruses, Baculovirus, phage λ, e.g. NM 989 or EMBL4, or phage M13, e.g. M13mp8, bacterial plasmids, e.g. pBR322, pUC18, or yeast plasmids, e.g. yeast 2µ plasmid, or a defective virus, phage or plasmid in the presence of a helper virus, phage or plasmid allowing replication of said defective virus, phage or plasmid, e.g. M13(+)KS vector in presence of e.g. M14K07 helper phage, or also chromosomal DNA, derived e.g. from filamentous fungi such as *Aspergillus spec.*, e.g. *A. niger*, for example those provided by EP 184 438. Preferred are vectors for *S. cerevisiae* or filamentous fungi, more preferably for *Aspergillus spec.*, even more preferably for *A. niger*.

A hybrid vector of the invention, including an expression vector, provides for replication of a desired DNA in a suitable host, either as an extrachromosomal element or by integration in the host chromosome. Several possible vector systems are available for integration and expression of the cloned DNA of the invention. In principle, all vectors which replicate and are stably maintained in the chosen host are suitable. Thus, the vector is selected depending on the host cells envisaged for transformation. In general, such host cells may be prokaryotic or eukaryotic microorganisms such as bacteria, fungi such as yeast, preferably *S. cerevisiae*, or as filamentous fungi preferably *Aspergillus spec.*, more preferably *A. niger*, or cells of higher eukaryotic origin such as vertebrate, for example mammalian, cells. Suitable host cells will be discussed in detail hereinbelow. A hybrid vector of the invention, including an expression vector, which is maintained as extrachromosomal element comprises an origin of replication (ori) or an autonomously replicating sequence (ARS), selectable marker sequences, and, optionally, additional restriction sites. A vector which is destinated for integration into a host chromosome needs not comprise an ori or ARS because it is replicated in the cell in connection with the chromosome.

An origin of replication or an autonomously replicating sequence (a DNA element which confers autonomously replicating capabilities to extrachromosomal elements) is provided either by construction of a vector including an exogeneous origin such as derived from Simian virus (SV 40) or another viral source, or by the host cell chromosomal mechanisms.

A hybrid vector of the invention, including an expression vector, may also contain selective markers depending on the host which is to be transformed, selected and cloned Any marker gene can be used which facilitates the selection of transformants due to the phenotypic expression of the marker. Suitable markers are particularly those expressing antibiotic resistance, e.g. against tetracycline or ampicillin, or, in the case of auxotrophic fungal mutants, genes which complement host lesions. Corresponding genes confer, for example, resistance to the antibiotic cycloheximide, or provide for prototrophy in an auxotrophic yeast, preferably *S.* cerevisiae, mutant, for example the ura3, leu2, his3 or trp1 gene. It is also possible to employ as markers structural genes which are associated with an autonomously replicating segment providing that the host to be transformed is auxotrophic for the product expressed by the marker.

Of particular importance in context with hybrid vectors, in particular expression vectors, for *A. niger* are marker genes which complement *A. niger* host lesions, such as the argB gene coding for the ornithine carbamoyl transferase, e.g. derived from *A. niger* or *A. nidulans* (EP 184 438), or *A. nidulans* DNA fragments homologous to the *N. crassa* pyr4 gene. Other suitable marker genes are described hereinafter in connection with the description of transformed hosts of the invention.

A hybrid vector of the invention suitable for the multiplication of DNA coding for Aspergillus-subtilisin in *E. coli* is, for example, plasmid pTZPEPC or pTZPEPD described hereinafter in the accompanying examples.

The term "expression cassette" in context of an expression vector of the present invention means a DNA sequence capable of expressing Aspergillus-subtilisin and comprises a promoter operatively linked with an Aspergillus-subtilisin coding region and optionally one or more further regulatory elements of the group consisting of a signal sequence, a transcriptional terminator, a transcriptional enhancer, a ribosomal binding site, a sequence for the efficient RNA processing, a sequence coding for efficient protein processing, and a sequence coding for correct protein localisation. In an expression cassette according to the present invention an Aspergillus-subtilisin coding region may be combined with homologous regulatory elements, i.e. such naturally linked therewith, or with heterologous regulatory elements, i.e. such derived from other genes.

A wide variety of promoter sequences may be employed, depending on the nature of the host cell. Promoters that are strong and at the same time well regulated are the most useful.

Examples for promoters arc the procaryotic $\lambda P_L$, $\lambda P_R$, *E. coli* lac, trp, or tac promoters. Promoters suitable for expression in yeast, preferably *S. cerevisiae*, are TRP1-, ADHI-, ADHII-, PHO3-, PHO5-, GAL10-, or glycolytic promoters such as the promoter of the enolase, glyceraldehyde-3-phosphate dehydrogenase, 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, or the PH05-GAPDH hybrid promoter (EP Appl. No. EP-A-213 593). Other examples for eukaryotic promotes are promoters derived from eukaryotic viruses, e.g. SV40, Rous sarcoma virus, adenovirus 2, bovine papilloma virus, papovavirus, cytomegalovirus derived promoters or mammalian cell derived promoters, e.g. of the actin, collagen, myosin, or β-globin gene. The eukaryotic promoters may be combined with enhancing sequences such as the yeast, preferably *S. cerevisiae*, upstream activating sequences (UAS) or viral or cellular enhancers such as the cytomegalovirus IE enhancers, SV40 enhancer, immunoglobulin gene enhancer or others.

Enhancers are transcription-stimulating DNA sequences, e.g. derived from viruses such as Simian virus, polyoma virus, bovine papilloma virus or Moloney sarcoma virus, or of genomic origin. An enhancer sequence may also be derived from the extrachromosomal ribosomal DNA of *Physarum polycephalum* (PCT/EP 8500278). Suitable enhancers are also, for example, upstream activation sites derived from the yeast acid phosphatase PH05 gene.

Signal sequences may be, for example, a presequence or secretory leader directing the secretion of the polypeptide, or the like. A signal sequence is, for example, a signal or leader peptide of Aspergillus-subtilisin, for example, the signal sequence shown in SEQ ID NO. 1. Further signal sequences are known from literature, e.g. those compiled in von Heijne, G., Nucleic Acids Res. 14, 4683 (1986).

Sequences necessary for the initiation and termination of transcription and for stabilizing the mRNA are commonly available from the noncoding 5'-regions and 3'-regions, respectively, of viral or eukaryotic cDNAs, e.g. from the expression host In an embodiment of the invention is an expression vector comprising an intron-less coding region composed of the two exons of the coding region shown in SEQ ID NO. 1 or of the four exons of the coding region shown in SEQ ID NO. 6 for expression of Aspergillus-subtilisin in procaryotes, e.g. in *E. coli*, or prefeably in yeast, more preferably in *S. cerevisiae* under the control of the GAL10 promoter, for example as in plasmid, pFBY138.

The invention preferably concerns an expression vector suitable for the expression of a DNA sequence encoding an Aspergillus-subtilisin in an Aspergillus strain.

One type of expression vector according to the invention comprises a DNA sequence encoding an Aspergillus-subtilisin, preferably of *A. niger*, under the control of a promoter which is naturally linked with the said DNA sequence, i.e. its homologous promoter. More preferred is an expression vector comprising a DNA sequence encoding PEPC of SEQ ID NO. 1, most preferably the DNA sequence shown in SEQ ID NO. 1, under the control of the promoter region shown in SEQ ID NO. 1 or an expression vector comprising a DNA sequence encoding PEPD of SEQ ID NO. 6, most preferably the DNA sequence shown in SEQ ID NO. 6, under the control of the promoter region shown in SEQ ID NO. 6. However, the PEPC coding region shown in SEQ ID NO. 1 may also be expressed under the control of the PEPD promoter shown in SEQ ID NO. 6, and vice versa.

Preferably the Aspergillus-subtilisin is secreted into the medium. This can be achieved by the use of a signal sequence which is functionally linked with the structural gene, preferably the signal sequence naturally linked with the Aspergillus-subtilisin structural gene, for example, as in plasmid pTZPEPC comprising the PEPC signal sequence and coding region shown in SEQ ID NO. 1 or as in plasmid pTZPEPD comprising the PEPD the signal sequence and coding region shown in SEQ ID NO. 6.

If such an expression vector is used for the expression of Aspergillus-subtilisin in a host strain of the species the Aspergillus-subtilisin gene is originally derived from, the Aspergillus-subtilisin is overexpressed because both the recombinant and the original Aspergillus-subtilisin gene are active under the same expression conditions.

Another type of expression vector of the invention comprises a DNA sequence coding for Aspergillus-subtilisin under the control of a promoter functional in Aspergillus, which is not naturally linked with the said DNA sequence. A promoters suitable for the expression of Aspergillus-subtilisin in *Aspergillus spec.*, in particular in *A. niger*, is, for example, a promoter of an *Aspergillus spec.* pectin lyase gene, preferably the promoter of the *A. niger* PLI (see EP-A-0 278 355), PLA, PLB, PLC, PLE or PLF (see EP-A-0 353 188) gene, a promoter of an *Aspergillus spec.* polygalacturonase gene, preferably the promoter of the *A. niger* PGI or PGII gene (see EP-Appl. EP-A-421919), a promoter of an *Aspergillus spec.* pyruvate kinase gene, preferably the promoter of the *A. niger* pki gene (EP-Appl. EP-A-439997), or also a promoter of an Aspergillus-subtilisin gene of the present invention, preferentially a promoter of an Aspergillus-subtilisin gene shown in SEQ ID NO. 1 or 6. Secretion of Aspergillus-subtilisin can also in this case be achieved by the use of a signal sequence which is functionally linked with the structural gene, for example the signal sequence naturally lined with the Aspergillus-subtilisin structural gene, for example, in the case of PEPC the signal sequence shown in SEQ ID NO. 1. However, also a signal sequence heterologous to the Aspergillus-subtilisin can be used, for example a signal sequence of an *Aspergillus spec.* pectin lyase gene, preferably the signal sequence of the *A. niger* PLI (see EP-A-0 278 355), PLA, PLB, PLC, PLE or PLF (see EP-A-0 353 188) gene, or a signal sequence of an *Aspergillus spec.* polygalacturonase gene, preferably the signal sequence of the *A. niger* PGI or PGII gene (see EP-Appl. EP-A-421919)

In a preferred embodiment of the invention, e.g. in the plasmid pPKIPEPCA, the pyruvate kinase promoter of *A. niger* is functionally linked with the coding region shown in SEQ ID NO. 1, encoding Aspergillus-subtilisin linked to its homologous signal sequence.

In another preferred embodiment of the invention, e.g. in the plasmid pPKIPEPCA, the pyruvate kinase promoter of *A. niger* is functionally linked with the coding region shown in SEQ ID NO. 6, encoding Aspergillus-subtilisin linked to its homologous signal sequence.

Process for the preparation of an Aspergillus-subtilisin gene

The invention also concerns a process for the preparation of a DNA molecule of the invention, i.e. such encoding an Aspergillus-subtilisin of the invention, preferably such encoding a preferred form of an Aspergillus-subtilisin of the invention, or for the preparation of a hybrid vector comprising such DNA molecule, said process comprising culturing a host transformed with a said DNA molecule or hybrid vector of the invention. In an alternative embodiment of the invention a DNA molecule of the invention can be prepared by chemical synthesis through nucleotide condensation The culturing of the hosts is carried out in a conventional nutrient medium which may be supplemented with or deprived of chemical compounds allowing negative or positive selection of the transformants, i.e. such hosts containing the desired DNA molecule together with a selection marker, from the non-transformants, i.e. such hosts lacking the desired DNA molecule.

Any transformable hosts useful in the art may be used, e.g. bacteria, such as *E. coli*, fungi, such as *Saccharomyces cerevisiae, Kluyveromyces lactis*, higher eukaryotic cells such as insect cells or mammalian cells, e.g. CHO cells, or in particular filamentous fungi, such as Aspergillus, e.g. *A. nidulans, A. oryzae, A. carbonarius, A. awamori* and especially *A. niger*. Transformation of the hosts is carried out by conventional methods.

A DNA sequence encoding Aspergillus-subtilisin can be obtained from the genome of an Aspergillus strain capable of expressing Aspergillus-subtilisin, or can be prepared, for example, by culturing a host which is transformed with a recombinant DNA molecule comprising a DNA sequence encoding an Aspergillus-subtilisin and, when required, isolating the desired DNA sequence therefrom.

In particular, such a DNA can be prepared by a method comprising a step selected from a) isolating genomic DNA from suitable Aspergillus cells, and selecting the desired DNA, e.g. using a DNA probe or using a suitable expression system and screening for expression of the desired polypeptide, b) isolating mRNA from suitable Aspergillus cells, selecting the desired mRNA, e.g. by hybridization with a DNA probe or by expression in a suitable expression system and screening for expression of the desired polypeptide, preparing single-stranded cDNA complementary to that mRNA, then double-stranded cDNA therefrom, c) isolating cDNA from a cDNA library and selecting the desired cDNA, e.g. using a DNA probe or using a suitable expression system and screening for expression of the desired polypeptide, d) synthesizing double stranded DNA in vitro by PCR technology of total Aspergillus DNA using oligonucleotide primers designed from the gene encoding *A. niger* pepC or *A. niger* pepD or other known serine proteases of the subtilisin type, or e) incorporating a double-stranded DNA obtainable according to step a), b), c) or d) into an appropriate vector, transforming a suitable host, multiplicating the host and isolating the DNA Genomic DNA may be isolated and screened for the desired DNA (step a). Genomic DNA is isolated from an Aspergillus strain capable of expressing an Aspergillus-subtilisin. A genomic DNA library is prepared therefrom by digestion with suitable restriction endonucleases and incorporation into suitable vectors following established procedures. The genomic DNA library is screened with a DNA probe as described hereinafter, or expressed in a suitable expression system and the obtained polypeptides screened in conventional manner.

A genomic library can be prepared e.g. by partial digestion of genomic DNA of an *A. niger* strain, e.g. NW756 or N400, with e.g. Sau3AI or MboI, and cloning the high molecular weight DNA fragments in a suitable host vector, e.g. the *E. coli* plasmid pUN121 or a lambda vector, e.g. EMBL4.

Other fungal strains producing a desired Aspergillus-subtilisin, for example, *A. japonicus, A. oryzae, A. nidulans, A. niger*, may serve as source for the genomic library and other suitable vectors, e.g. those mentioned hereinbefore, may be used as recipient for the fragments.

In order to successfully screen the genomic library for DNA sequences coding for Aspergillus-subtilisin a hybridizing DNA probe is necessary. This can be a synthetic DNA probe if the amino acid sequence or part thereof of a desired Aspergillus-subtilisin is known, or another subtilisin gene, e.g. from yeast, or a part thereof, which hybridizes to an Aspergillus-subtilisin gene.

Polyadenylated messenger RNA (step b) is isolated from the suitable cells, by known methods. Isolation methods involve, for example, homogenizing in the presence of a detergent and a ribonuclease inhibitor, e.g. heparin, guanidinium isothiocyanate or mercaptoethanol extracting the mRNA with suitable chloroform-phenol mixtures, optionally in the presence of salt and buffer solutions, detergents and/or cation chelating agents, and precipitating mRNA from the remaining aqueous, salt-containing phase with ethanol, isopropanol or the like. The isolated mRNA may be further purified by centrifuging in a cesium chloride gradient followed by ethanol precipitation and/or by chromatographic methods, e.g. affinity chromatography, for example chromatography on oligo(dT) cellulose or on oligo(U) sepharose. Preferably, such purified total mRNA is fractionated according to size by gradient centrifugation, e.g. in a linear sucrose gradient, or chromatography on suitable size fractionation columns, e.g. on agarose gels.

The desired mRNA is selected by screening the mRNA directly with a DNA probe, or by translation in suitable cells or cell-free systems and screening the obtained polypeptides.

The selection of the desired mRNA is preferably achieved using a DNA hybridization probe as described hereinafter, thereby avoiding the additional step of translation. Suitable DNA probes are DNAs of known nucleotide sequence, for example synthetic DNAs, cDNAs derived from mRNA coding for the desired polypeptides, or genomic DNA fragments comprising e.g. adjacent DNA sequences which are isolated from a natural source or from a genetically engineered microorganism.

Fractionated mRNA may be translated in cells, e.g. frog oocytes, or in cell-free systems, e.g. in reticulocyte lysates or wheat germ extracts. The obtained polypeptides are screened for enzymatic activity or for reaction with antibodies raised against the native polypeptide, e.g. in an immunoassay, for example radioimmunoassay, enzyme immnoassay or immunoassay with fluorescent markers. Such immunoassays and the preparation of polyclonal and monoclonal antibodies are well known in the art and are applied accordingly.

The preparation of a single-stranded complementary DNA (cDNA) from the selected mRNA template is well known in the art, as is the preparation of a double-stranded DNA from a single-stranded DNA. The mRNA template is incubated with a mixture of deoxynucleoside tiphosphates, optionally radioactively labelled deoxynucleoside triphosphates (in order to be able to screen the result of the reaction), a primer sequence such as an oligo-dT residue hybridizing with the poly(A) tail of the mRNA and a suitable enzyme such as a reverse transcriptase e.g. from avian myeloblastosis virus (AMV). After degradation of the template mRNA e.g. by alkaline hydrolysis, the cDNA is incubated with a mixture of deoxynucleoside triphosphates and a suitable enzyme to give a double-stranded DNA. Suitable enzymes are for instance a reverse transcriptase, the Klenow fragment of *E. coli* DNA polymerase I or T4 DNA polymerase. Usually, a hairpin loop structure formed spontaneously by the single-stranded cDNA acts as a primer for the synthesis of the second strand. This hairpin structure is removed by digestion with S1 nuclease. Alternatively, the 3'-end of the single-stranded DNA is first extended by homopolymeric deoxynucleotide tails prior to the hydrolysis of the mRNA template and the subsequent synthesis of the second cDNA strand.

In the alternative, double-stranded cDNA is isolated from a cDNA library and screened for the desired cDNA (step c). The cDNA library is constructed by isolating mRNA from suitable cells, and preparing single-stranded and double-stranded cDNA therefrom as described above. This cDNA is digested with suitable resctriction endonucleases and incorporated into λ phage, e.g. λ charon 4A or λ gt11 following established procedures. The cDNA library replicated on nitrocellulose membranes is screened by using a DNA probe as described hereinbefore, or expressed in a suitable expression system and the obtained polypeptides screened for reaction with an antibody specific for the desired compounds.

Another method for the preparation of double stranded DNA is PCR technology (step d). This method can in particular be used for the preparation of a large amount of double stranded DNA starting from a small amount of DNA or RNA with at least partly known sequences. However, also a DNA insert with unknown sequence which is flanked by known vector sequences can be used as starting material. In PCR technology DNA molecules, e.g. oligonucleotides, are used as primer for the enzymatic template-dependent synthesis of DNA. Large amounts can be prepared because the denaturing of double stranded DNA, hybridisation with the primers, and enzymatic synthesis can be sequentially repeated. The number of synthesized DNA molecules increases exponentially because it doubles each round. PCR technology is state of the art and can be conventionally applied in the present invention. The oligonucleotide primer can be designed to hybridize to DNA that would encode conserved subtilisin-type serine protease protein sequences based on comparisons between known serine proteases of the subtilisin-type. PCR technology is well known in the art and conventional PCR techniques may be applied to the present invention, e.g. those described in: M. A. Innis et al. (eds.), PCR protocols. A guide to methods and applications. Academic Press, San Diego (1990).

A variety of methods are known in the art for the incorporation of double-stranded cDNA or genomic DNA into an appropriate vector (step e). For example, complementary homopolymer tracts may be added to the double-stranded DNA and the vector DNA by incubation in the presence of the corresponding deoxynucleoside triphosphates and an enzyme such as terminal deoxynucleotidyl transferase. The vector and double-stranded DNA are then joined by base pairing between the complementary homopolymeric tails and finally ligated by specific joining enzymes such as ligases. Other possiblities are the addition of synthetic linkers to the termini of the double-stranded DNA, or the incorporation of the double-stranded DNA into the vector by blunt- or staggered-end ligation. Appropriate vectors will be discussed in detail hereinbelow.

Transformation procedures for transforming appropriate host cells with the obtained hybrid vector and the selection and multiplication of transformed host cells are well known in the art. Examples for such methods are given further below.

The isolation of the desired DNA, mutants and fragments therof according to the invention is achieved by methods known in the art, e.g. extraction with phenol and/or chloroform. Optionally, the DNA can be further manipulated e.g. by treatment with mutagenic agents to obtain mutants, or by digestion with restriction enzymes to obtain fragments, modify one or both termini to facilitate incorporation into the vector, remove intervening sequences and the like.

The nucleotide sequence of a DNA according to the invention can be determined by methods known per se, for example by the Maxam-Gilbert method using end-labelled DNA or by the dideoxy chain termination method of Sanger.

Aspergillus-subtilisin gene sequences of the present invention can also be prepared by an in vitro synthesis according to conventional methods. The in vitro synthesis is especially applicable for the preparation of smaller fragments of an Aspergillus-subtilisin gene coding for fragments of Aspergillus-subtilisin with serine protease activity. In vitro synthesis is also particularly applicable for the synthesis of DNA coding for a promoter or a signal peptide. The in vitro synthesis is preferably applied to the Aspergillus-subtilisin gene derived from *A. niger* or fragments thereof, most preferably to the pepC gene shown in SEQ ID NO. 1 or the promoter or signal sequence thereof or to the pepD gene shown in SEQ ID NO. 6 or the promoter or signal sequence thereof.

Suitable methods for the synthesis of DNA have been presented in summary form by S. A. Narang (Tetrahedron 39, 3, 1983). The known synthesis techniques allow the preparation of polynucleotides up to 120 bases in length, in good yield, high purity and in a relatively short time. Suitably protected nucleotides are linked with one another by the phosphodiester method (K. L. Agarwal et al., Angew. Chemie 84, 489, 1972), the more efficient phosphotriester method (C. B. Reese, Tetrahedron 34, 3143, 1972), the phosphite triester method (R. L. Letsinger et al., J. Am. Chem. Soc. 98, 3655, 1976) or phosphoramidite method (S. L. Beaucage and M. H. Carruthers, Tetrahedron 22, 1859, 1981). Simplification of the synthesis of the oligonucleotides and polynucleotides is made possible by the solid phase method, in wich the nucleotide chains are bound to a suitable polymer. The actual double-stranded DNA is built up enzymatically from chemically prepared overlapping oligonucleotides from both DNA stands, which are held together in the correct arrangement by base-pairing and are then chemically linked by the enzyme DNA ligase. Another possibility comprises incubating overlapping single oligonucleotides from the two DNA strands in the presence of the four required deoxynucleoside triphosphates with a DNA polymerase, for example DNA polymerase I, the Klenow fragment of polymerase I or T4 DNA polymerase, or with AMV (avian myeloblastosis virus) reverse transcriptase, The two oligonucleotides are thereby held together in the correct arrangement by base-pairing and are supplemented with the required nucleotides by the enzyme to give a complete double-stranded DNA (S. A. Narang et al., Anal. Biochem. 121, 356, 1982).

In performing the present invention, a subtilisin gene of another species, e.g. yeast, or a fragment thereof can be used as probe for identifying an *Aspergillus spec.*, e.g. an *A. niger*, subtilisin mRNA in an RNA fraction or a subtilisin DNA in a genomic or cDNA library. From the primary sequence of the *A. niger* gene and comparison to other proteases the coding region of the protease can be deduced and the relationship of the gene to the subtilisin gene family can be confirmed. The gene obtained can be used for the preparation of recombinant protease as outlined in detail hereinbelow.

Synthetic DNA probes are synthesized according to known methods as detailed hereinbelow, preferably by stepwise condensation using the solid phase phosphotriester, phosphite triester or phosphoramidite method, e.g. the condensation of dinucleotide coupling units by the phosphotriester method. These methods are adapted to the synthesis of mixtures of the desired oligonucleotides by using mixtures of two, three or four nucleotides dA, dC, dG and/or dT in protected form or the corresponding dinucleotide coupling units in the appropriate condensation step as described by Y. Ike et al. (Nucleic Acids Research 11, 477, 1983).

For hybridization, the DNA probes are labelled, e.g. radioactively labelled by kinase reaction. The hybridization of the size-fractionated mRNA with the DNA probes containing a label is performed according to known procedures, i.e. in buffer and salt solutions containing adjuncts, e.g. calcium chelators, viscosity regulating compounds, proteins, non-homologous DNA and the like, at temperatures favoring selective hybridization, e.g. between 0° C. and 80° C., for example between 25° C. and 50° C. or around 65° C., preferably at around 20° lower than the hybrid double-stranded DNA melting temperature.

Transformed hosts and preparation thereof

Furthermore, the invention concerns host cells transformed with a hybrid or expression vector of the invention, preferably such encoding the preferred forms of the Aspergillus-subtilisin of the invention.

Examples of suitable hosts, particularly for multiplication of the recombinant DNA molecules of the invention, are microorganisms which are devoid of or poor in restriction enzymes or modification enzymes, such as bacteria, in particular strains of *Escherichia coli*, for example *E. coli* X1776, *E. coli* Y1090, *E. coli* W3110, *E. coli* HB101/ LM1035, *E. coli* JA 221, *E. coli* DH5α, or preferentially *E. coli* DH5αF', JM109, MH1 or HB101, or *E. coli* K12 strain. Suitable hosts are also other procaryotic cells, e.g. *Bacillus subtilis*, *Bacillus stearothermophilus*, Pseudomonas, Haemophilus, Streptococcus and others, and yeasts, for example *Saccharomyces cerevisiae* such as *S. cerevisiae* GRF 18. Further suitable host cells are cells of higher organisms, in particular established continuous human or animal cell lines, e.g. human embryonic lung fibroblasts L132, human malignant melanoma Bowes cells, HeLa cells, SV40 virus transformed kidney cells of African green monkey COS-7 or Chinese hamster ovary (CHO) cells.

Examples of suitable cells for the expression of an Aspergillus-subtilisin gene of the invention are the cells mentioned hereinbefore transformed with an appropriate expression vector and additionally suitable insect cells transformed with an appropriate Baculovirus expression vector, and, in particular, filamentous fungi, for example Penicillium, Cephalosporium or preferentially *Aspergillus spec.*, e.g. *A. carbonarius, A. awamori, A. nidulans, A. oryzae* or more preferentially *A. niger*, transformed with an appropriate expression vector.

The invention concerns also a method for the preparation of such transformants comprising treatment of a suitable host cell under transforming conditions with a DNA molecule or hybrid vector of the invention, optionally together with a selection marker gene and optionally selecting the transformants. The Aspergillus-subtilisin gene may also become integrated into the host genome after tranformation, in particular if eukaryotic cells, for example *Aspergillus spec.* is used as host.

Transformation of microorganisms is carried out according to conventional methods as described in the literature, for example for *S. cerevisiae* (A. Hinnen et al., Proc.Natl.Acad.Sci.USA, 75, 1929,1978), for *B. subtilis* (Anagnostopoulos et al., J. Bacteriol. 81, 741, 1961), for *E. coli* (M. Mandel et al., J. Mol. Biol. 53, 159, 1970), and for Aspergillus [F. Buxton et al., Gene 37:207–14(1985), D. J. Balance et al., Biochem. Biophys. Res. Commun. 112:284–9 (1983)]

Accordingly, the tansformation procedure of *E. coli* cells includes, for example, $Ca^{2+}$ pretreatment of the cells so as to allow DNA uptake, and incubation with the hybrid vector. The subsequent selection of the transformed cells can be achieved, for example, by transferring the cells to a selective growth medium which allows separation of the transformed cells from the parent cells dependent on the nature of the marker sequence of the vector DNA. Preferably, a growth medium is used which does not allow growth of cells which do not contain the hybrid vector.

The transformation of fungi such as yeast or *Aspergillus spec.* comprises, for example, steps of enzymatic removal of the cell wall by means of glucosidases, treatment of the obtained spheroplasts with the hybrid vector in the presence of polyethylene glycol and $Ca^{2+}$ ions, and regeneration of the cell wall by embedding the spheroplasts into agar. Preferably, the regeneration agar is prepared in a way to allow regeneration and selection of the transformed cells as described above at the same time.

Transformation of cells of higher eukaryotic origin, such as mammalian cell lines, is preferably achieved by transfection. Transfection is carried out by conventional techniques, such as calcium phosphate precipitation, microinjection, protoplast fusion, electroporation, i.e. introduction of DNA by a short electrical pulse which transiently increases the permeability of the cell membrane, or in the presence of helper compounds such as diethylaminoethyldextran, dimethyl sulfoxide, glycerol or polyethylene glycol, and the like. After the transfection procedure, transfected cells are identified and selected e.g. by cultivation in a selective medium chosen depending on the nature of the selection marker, for example standard culture media such as Dulbecco's modified Eagle medium (DMEM), minimum essential medium, RPMI 1640 medium and the like, containing e.g. the corresponding antibiotic.

The transformed host cells are cultured by methods known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

The medium is preferably chosen so as to exert a selection pressure and prevent the growth of cells which have not been transformed or have lost the hybrid vector. Thus, for example, an antibiotic is added to the medium if the hybrid vector contains an antibiotic resistance gene as marker. If, for instance, a host cell is used which is auxotrophic in an essential amino acid whereas the hybrid vector contains a gene coding for an enzyme which complements the host defect, a minimal medium deficient in said amino acid is used to culture the transformed cells.

Cells of higher eukaryotic origin such as mammalian cells are grown under tissue culture conditions using commercially available media, for example Dulbecco's modified Eagle medium (DMEM), minimum essential medium, RPMI 1640 medium and the like as mentioned above, optionally supplemented with growth-promoting substances and/or mammalian sera. Techniques for cell cultivation under tissue culture condition are well known in the art and include homogeneous suspension culture, e.g. in an airlift reactor or in a continuous stirrer reactor, or immobilized or entrapped cell culture, e.g. in hollow fibres, microcapsules, on agarose microbeads, porous glass beads, ceramic cartridges, or other microcarriers.

Culturing is effected by processes which are known in the art. The culture conditions, such as temperature, pH value of the medium and fermentation time, are chosen so that a maximum titer of the polypeptide or derivative of the invention is obtained. Thus, an E. coli or yeast strain is preferably cultured under aerobic conditions by submerged culture with shaking or siring at a temperature of about 20° C. to 40° C., preferably at about 30° C., and a pH value of 4 to 8, preferably of about pH 7, for about 4 to 30 hours, preferably until maximum yields of the polypeptide or derivative of the invention are reached.

In order to allow selection of the transformed from the nontransformed cells, the DNA molecules of the invention carry a selection marker or, alternatively, the cells are cotransformed with a second vector containing such marker. As in other systems such selection marker is an expressible, structural gene, the expressed polypeptide of which (an enzyme) provides resistance against compounds toxic to the receipt organism or which completes the enzyme system of a mutant lacking such essential polypeptide. Such marker genes suitable for selection of transformed filamentous fungal cells are, for example, the known qa-2, pyrG4, trpC, amdS or argB genes.

As described in EP-A-0 278 355 a marker gene, named pyrA, was isolated from the genomic library of A. niger, which is related to and has similar function as pyrG of A. nidulans and pyr4 of N. crassa, namely producing the enzyme orotidine 5'-phosphate decarboxylase. This enzyme catalyses the decarboxylation of orotidine 5'-phosphate to uridylic acid (uridine 5'-phosphate) and also of fluoro-orotic acid to the toxic fluoro-uridine. However, DNA of any other pyr gene coding for orotidine-5'-phosphate decarboxylase may be used. From a positive clone named E. coli BJ5183/pCG59D7 (DSM 3968), the plasmid pCG59D7, comprising the pyrA gene, was isolated and used for cotransformation of an A. niger pyrA⁻ mutant. Such pyrA⁻ mutant is defective in the orotidine 5'-phosphate decarboxylase gene and therefore is unable to produce the corresponding enzyme. Such mutant was prepared by treating conidiospores of A. niger N756 under mutating UV-irradiation and colonies surviving in the presence of fluoro-orotic acid and uridine are selected. Colonies surviving in the presence of fluoroorotic acid and absence of uridine are eliminated The remaining uridine-requiring mutants, according to their ability of being tansformable, belong to two complementation groups pyrA and pyrB, represented by A. niger mutants An8 and An10, respectively. They are treated in the form of protoplasts thereof under tansforming condition with the pyrA containing plasmid pCG59D7 (DSM 3968). Only the A. niger An8 (DSM 3917) colonies were found to be transformed and to contain the pyrA gene as evidenced by the hybridizing ability of digested DNA thereof with DNA of pUN 121.

Process for the preparation of Aspergillus-subtilisin

The invention also concerns a process for the preparation of an Aspergillus-subtilisin of the invention, preferably the preferred forms thereof, comprising culturing a host transformed with an expression vector of the invention under conditions suitable for the expression of the Aspergillus-subtilisin gene. When required, the polypeptide is isolated in conventional manner. Depending on the construction of the expression vector, Aspergillus-subtilisin is either produced or, if a signal sequence is present, produced and secreted.

Whether a selected host is suitable for the expression or not depends mainly on the regulatory sequences chosen for constructing the expression vector, in particular on the promoter.

For example, if a promoter derived from an Aspergillus, preferably A. niger, gene is used for the expression of an Aspergillus-subtilisin gene of the invention, an Aspergillus strain, preferably A. niger, is a suitable host. However, if a promoter not derived from an Aspergillus gene is used for the construction of an expression vector of the invention, other hosts are suitable for the expression, e.g. bacteria such as E. coli, or yeast, such as S. cerevisiae. Suitable hosts and promoters for the preparation of polypeptides according to the invention are also those suitable for transformation given hereinbefore.

In particular, the invention concerns a process in which a transformed Aspergillus host is expressing the exogenous Aspergillus-subtilisin gene under conditions in which endogenous Aspergillus-subtilisin genes are active and thus expressing more than the natural amount of Aspergillus-subtilisin due to the increased gene dose. For this purpose, the Aspergillus host, in particular A. niger, is transformed with an expression vector comprising an Aspergillus-subtilisin gene under the control of its homologous, i.e. naturally linked, expression control sequences, in particular promoter and signal sequence.

In particular, the invention also concerns a process in which a transformed Aspergillus host is expressing the exogenous Aspergillus-subtilisin gene to a higher level or under different conditions than the endogenous gene because it is fused to a different promoter.

The conditions for maximal expression of the exogenous gene or genes depend on the selected expression system. For example, if a promoter of a pectin lyase (PL) or of a polygalacturonase (PG) gene of A. niger is used, the expression of the Aspergillus-subtilisin gene linked therewith is inducible in an A. niger cell by addition of pectin or pectin degradation products to the culture medium. In the presence of sufficient glucose, however, the promoter is not inducable, if an A. niger strain, e.g. An8 (DSM 3917), is used as host. This means, an Aspergillus-subtilisin gene under the control of an A. niger PL or PG promoter is "catabolite repressed" in A. niger. However, if another Aspergillus strain is used, preferentially A. oryzae or most preferentially A. nidulans, an Aspergillus-subtilisin gene under the control of an A. niger PL or PG promoter is expressed constitutively, i.e. also in the absence of pectin and/or in the presence of glucose. It can therefore be advantageous to express an Aspergillus-subtilisin gene under the control of an A. niger PL or PG promoter in an Aspergillus host other than A. niger, preferentially A. oryzae or most preferentially A. nidulans, because, for example, glucose instead of pectin can be added to the nutrient medium as energy and carbon source during the expression of the gene.

If an Aspergillus, preferably A. niger, pyruvate kinase promoter is used for the expression of an Aspergillus-subtilisin gene, the gene is expressed if a minimal medium with glucose as carbon- and energy source is used.

It is now possible to overexpress Aspergillus-subtilisin, whereby various methods can be applied. A purified single Aspergillus-subtilisin can be prepared by a method in which a suitable host which is not capable of expressing any Aspergillus-subtilisin or which expresses Aspergillus-subtilisin in low amount or which does not express Aspergillus-subtilisin under the induction conditions used for the expression of the exogenous Aspergillus-subtilisin gene, is transformed with a hybrid vector comprising a structural gene coding for an Aspergillus-subtilisin, prefeably from A. niger, most preferably PEPC shown in SEQ ID NO. 1, or a fragment of an Aspergillus-subtilisin serine protease activity, and that said structural gene is expressed. If a host not capable of expressing any Aspergillus-subtilisin is used, the respective single Aspergillus-subtilisin can be obtained in pure form, that means uncontaminated by any other Aspergillus-subtilisin.

A host not capable of expressing any Aspergillus-subtilisin is either a microorganism having no corresponding gene or an Aspergillus strain whose expression of endogeneous Aspergillus-subtilisin genes are suppressed in an appropriately conditioned growth medium, whereas the exogenous Aspergillus-subtilisin promoter operatively linked with the desired Aspergillus-subtilisin structural gene, e.g. an A. niger derived promoter, is active under these conditions or where the Aspergillus-subtilisin gene is fused to another promoter.

Other promoters and strains suitable for the preparation of Aspergillus-subtilisin are the given hereinbefore in the description of the expression vectors of the invention.

Aspergillus-subtilisin and use thereof

The invention also concerns a pure Aspergillus serine protease of the subtilisin type per se, herein named "Aspergillus-subtilisin". Such a protease is understood as (a) being derived from Aspergillus spec., (b) exhibiting protease activity due to a catalytic serine residue at the active site and (c) having sufficient amino acid sequence homology with known serine proteases for being grouped into the subtilisin family. Included within the term Aspergillus-subtilisin are also fragments of such an enzyme which retain serine protease activity.

The invention concerns preferentially a pure Aspergillus-subtilisin of Aspergillus niger, preferably the serine protease PEPC having the amino acid sequence shown in the sequence listing under SEQ ID. NO. 1 or the serine protease PEPD having the amino acid sequence shown in the sequence listing under SEQ ID NO. 6, and fragments and mutants thereof which retain serine protease activity.

The invention concerns further enzymatic compositions comprising one or more of an Aspergillus-subtilisin and/or a derivative thereof with serine protease activity and/or biologically acceptable salts thereof optionally in a predetermined combination with one or more suitable enzymes having other than Aspergillus-subtilisin activity.

Aspergillus strain deficient in Aspergillus-subtilisin

The invention also concerns a mutated Aspergillus strain, preferably a mutated A. niger strain, deficient in an endogenous Aspergillus-subtilisin gene. Preferred is an A. niger strain deficient in the pepC gene shown in SEQ ID NO. 1 or in the pepD gene shown in SEQ ID NO. 6. Preferred is also an A. niger strain deficient in both the pepC and pepD gene.

A mutated Aspergillus strain of the invention having a defective Aspergillus-subtilisin gene can in a preferred embodiment of the invention be prepared by gene disruption, i.e. a DNA sequence corresponding to the endogenous Aspergillus gene which is desired to be destroyed is in vitro mutated to a defective gene and transformed into the Aspergillus host cell. Due to a homologous recombination event in the cell the intact endogenous gene is replaced by the defective exogenous one. Usually the exogenous gene is destroyed by inserting a marker gene into the coding region. This leads to a defective gene which can be easily monitored and used for selecting transformants with the corresponding endogenous gene disrupted. However, also other methods for mutagenesis may be used for the preparation of a mutated Aspergillus strain, preferably a mutated A. niger strain, in which an endogenous Aspergillus-subtilisin gene is mutated in such way that no functional Aspergillus-subtilisin can be expressed.

In a most preferred embodiment of the invention an A. niger strain is transformed with a hybrid vector comprising a defective mutant of the pepC gene shown in SEQ ID NO. 1, e.g. a disrupted pepC gene having a selection marker gene inserted, e.g. as comprised in plasmid pPEPCPYRA described in the accompanying examples, and transformants are selected.

In another most preferred embodiment of the invention an A. niger strain is transformed with a hybrid vector comprising a defective mutant of the pepD gene shown in SEQ D NO. 6, e.g. a disrupted pepD gene having a selection marker gene inserted e.g. as comprised in plasmid pPEPDPYRA described in the accompanying examples, and transformants are selected.

In a third most preferred embodiment of the invention an A. niger strain is transformed with a defective mutant of the pepC gene shown in SEQ ID NO. 1, e.g. a disrupted pepC gene having a selection marker gene inserted, e.g. as comprised in plasmid pPEPCPYRA described in the accompanying examples, and with a defective mutant of the pepD gene shown in SEQ ID NO. 6, e.g. a disrupted pepD gene having a selection marker gene inserted, e.g. as comprised in plasmid pPEPDPYRA described in the accompanying examples, and transformants defective in both pepC and pepD are selected A mutated Aspergillus strain of the invention having a defective Aspergillus-subtilisin gene is useful for the expression of an improved production of heterologous or homologous proteins either intra- or extracellularly.

The expression of heterologous or homologous proteins in *Aspergillus spec.* can be achieved according to conventional methods. Usually, an expression vector is constructed comprising a homologous or heterologous gene operably linked with a homologous or heterologous promoter functional in Aspergillus and optionally with other expression control sequences functional in Aspergillus, e.g. those defined hereinbefore. When required the polypeptide is isolated in a conventional manner. Depending on the construction of the expression vector the products are either produced in the host cell or, if a signal sequence is present, are produced in the cell and secreted.

Structural genes in this context are, for example, structural genes which originate from viruses, procaryotic cells or eucaryotic cells and which may be derived from genomic DNA or from cDNA prepared via the mRNA route or may be synthesized chemically, coding for a wide variety of useful polypeptides, including glycosylated polypeptides, in particular of higher eukaryotic, especially mammalian, such as animal or especially human origin, such as enzymes which can be used, for example, for the production of nutrients and for performing enzymatic reactions in chemistry, or polypeptides, which are useful and valuable for the treatment of human and animal diseases or for the prevention thereof, for example, hormones, polypeptides with immunomodulatory, anti-viral and anti-tumor properties, antibodies, viral antigens, vaccines, clotting factors, foodstuffs and the like.

Examples of such structural genes are e.g. those coding for Aspergillus polygalacturonase, e.g. PGI or PGII, or Aspergillus pectin lyase, e.g. PLI, PLA, PLB, PLC, PLE and PLF, or hormones such as secretin, thymosin, relaxin, calcitonin, luteinizing hormone, parathyroid hormone, adrenocorticotropin, melanoycte-stimulating hormone, β-lipotropin, urogastrone or insulin, growth factors, such as epidermal growth factor, insulin-like growth factor (IGF), e.g. IGF-I and IGF-II mast cell growth factor, nerve growth factor, glia derived nerve cell growth factor, or transforming growth factor (TGF), such as TGFβ, growth hormones, such as human or bovine growth hormones, interleukin such as interleukin-1 or -2, human macrophage migration inhibitory factor (MIF), interferons, such as human α-interferon, for example interferon-αA, αB, αD or αF, β-interferon, γ-interferon or a hybrid interferon, for example an αA-αD- or an αB-αD-hybrid interferon, especially the hybrid interferon BDBB, proteinase inhibitors such as $\alpha_1$-antitrypsin, SLPI and the linke, hepatitis virus antigens, such as hepatitis B virus surface or core antigen or hepatitis A virus antigen, or hepatitis nonA-nonB antigen, plasminogen activators, such as tissue plasminogen activator or urokinase, tumour necrosis factor, somatostatin, renin, β-endorphin, immunoglobulins, such as the light and/or heavy chains of immunoglobulin D, E or G, or human-mouse hybrid immunoglobulins, immunoglobulin binding factors, such as immunoglobulin E binding factor, calcitonin, human calcitonin-related peptide, blood clotting factors, such as factor IX or VIIIc, erythropoietin, eglin, such as eglin C, hirudin, desulfatohirudin, such as desulfatohirudin variant HV1, HV2 or PA, human superoxide dismutase, viral thymidin kinase, β-lactamase, glucose isomerase. Preferred genes are those coding for a human α-interferon or hybrid interferon, particularly hybrid interferon BDBB, human tissue plasminogen activator (t-PA), hepatitis B virus surface antigen (HBVsAg), insulin-like growth factor I and II, eglin C and desulfatohirudin, e.g. variant HV1.

The most preferred embodiments are those described in the accompanying examples.

EXAMPLES

The following examples serve to illustrate the invention, however, are in no way intended to restrict it.

The abbreviations have the following meanings:

| | |
|---|---|
| BSA | bovine serum albumin |
| DTT | 1,4-dithiothreitol |
| EDTA | ethylenediamine tetra acetic acid, disodium salt |
| IPTG | isopropyl-β-D-thiogalactopyranoside |
| kbp | kilo base pairs |
| PEG | polyethylene glycol |
| SDS | sodium dodecyl sulfate |
| Tris | tris (hydroxymethyl) aminomethane |
| X-gal | 5-bromo-4-chloro-3 indolyl-β-galactoside |

Buffers, media, reagents

| | |
|---|---|
| SM | 100 mM NaCl, 8.1 mM $MgSO_4$, 50 mM Tris-HCl pH 7.5, 0.01% gelatin |
| LB | 1% trypticase peptone (BBL), 0.5% yeast extract (BBL), 1% NaCl and 0.5 mM Tris-HCl pH 7.5 |
| LM | 1% trypticase peptone (BBL), 0.5% yeast extract (BBL), 10 mM NaCl and 10 mM $MgCl_2$ |
| SSC | 0.15M NaCl, 0.015M tri-sodium citrate |
| PSB | 10 mM Tris-HCl, pH 7.6, 100 mM NaCl, 10 mM $MgCl_2$, |
| TE | 10 mM Tris-HCl pH 8.0, 0.1 mM EDTA pH 8.0 |
| minimal medium | 1 liter contains 1.5 g $KH_2PO_4$, 0.5 g KCl, 0.5 g $MgSO_4.7H_2O$, 0.9 mg $ZnSO_4.7H_2O$, 0.2 mg $MnCl_2.4H_2O$, 0.06 mg $CoCl_2.6H_2O$, 0.06 mg $CuSO_4.5H_2O$, 0.29 mg $CaCl_2.62H_2O$, 0.2 mg $FeSO_4.7H_2O$, nitrogen and carbon sources as specified in the text or 6 g $NaNO_3$ and 10 g glucose per liter if these sources are not explicitly mentioned, adjusted to pH 6.0 with NaOH |
| complete medium | minimal medium with 6 g $NaNO_3$ and 10 g glucose per liter, plus per liter 2 g trypicase peptone (BBL), 1 g casaminoacids (Difco), 1 g yeast extract (BBL), 0.5 g ribonucleic acid sodium salt from yeast (ICN, Cleveland, USA), 2 ml vitamin solution, adjusted to pH 6.0 with NaOH |
| vitamin solution | per 100 ml 10 mg thiamine, 100 mg riboflavin, 10 mg panthotenic acid, 2 mg biotin, 10 mg p-aminobenzoic acid, 100 mg nicotinamide, 50 mg pyridoxin-HCl |
| TBE | 1 liter contains 4 ml of a 0.5M EDTA pH 8.0 solution, 10.8 g Tris and 5.5 g $H_3BO_3$ |
| phenol | phenol treated as described by Maniatis et al., Molecular Cloning; A Laboratory Manual, Cold Spring Harbour Laboratory 1982 (p438) |
| sample buffer | 10% (v/v) glycerol, 100 mM EDTA pH 8.0 and 0.01% bromophenol blue |
| RNase A | RNase A treated as described by Maniatis et al., Molecular Cloning; A Laboratory Manual, Cold Spring Harbour Laboratory 1982 (p451) |

The following strains and vectors are used:

| | |
|---|---|
| *A. niger* N400 | wild type. |
| *A. niger* An8 | uridine auxotrophic mutant of the pectinase complex highly producing strain *A. niger* N756, disclosed in EP-A-0 278 355, deposited as DSM 3917. |
| *E. coli* LE392 | F⁻, hsdR514 ($r_k^-$, $m_k^+$), supE44, supF58, lacY1, or (lac1ZY)6, galK2, galT22, metB1, trpR55, λ⁻. |
| *E. coli* DH5αF' | F', endA1, hsdR17, ($r_k^-$, $m_k^+$), supE44, thi-1, recA1, gyrA, relA1, )80Ølac Z M15, Δ(lac ZYA-argF)U169, λ⁻. |

| | |
|---|---|
| EMBL4 | EMBL4 is a lambda replacement vector with a cloning capacity of 9–23 kbp (Frischauf et al., J. Mol Biol. 170:827–842, 1983). It contains a multiple cloning region between the lambda arms and the nonessential stuffer region. This allows multiple restriction enzyme digestions to be performed in a manner such that religation of the stuffer to the vector arms is reduced as the foreign DNA of interest is inserted. The vector also makes use of the Spi phenotype to provide a direct selection for recombinants (Zissler et al., in: A. D. Hershey (ed.) The Bacteriophage lambda, Cold Spring Harbour Laboratory, 1971). |

Example 1

Construction of a genomic library of *Aspergillus niger*

Example 1.1: Isolation of high molecular weight DNA from *A. niger* N400

Conidiospores of *Aspergillus niger* strain N400 are inoculated in 200 ml minimal medium to a final spore density of $10^6$ spores/ml and shaken in 11 Erlenmeyers for 24 h at 28° C. at 300 rpm. The mycelium is harvested by filtration through Myracloth on a Buchner funnel, washed with cold sterile saline, frozen in liquid nitrogen and either stored at −60° C. or used directly. The method used for isolation of DNA to prepare the genomic library is based on the procedure described by Yelton et al. [Proc. Natl. Acad. Sci. USA 81:1470–1474(1984)].

For library construction, 10 g mycelium is ground in liquid nitrogen in 1 g portions in a Braun microdismembrator. The ground mycelium is transferred to a 11 sterile erlenmeyer, containing 200 ml extraction buffer (50 mM EDTA pH 8.5, 0.2% SDS) and 200 µl diethylpyrocarbonate. The mixture is slowly warmed up to room temperature and then heated for 20 min to 68° C. with occasional shaking. The suspension is cooled to room temperature and centrifuged for 15 min at 12,000× g. 1/16 volume of an 8M potassium acetate solution pH 4.2 is added to the supernatant and the mixture is left on ice for 1 h. The precipitate is removed by centrifugation (20 min.; 16,000× g; 4° C.). The nucleic acids are precipitated from the supernatant by an incubation with 0.6 volume of isopropanol on ice for 15 min. The precipitated nucleic acid is collected by centrifugation (10 min.; 6,000× g; 4° C.), washed with 70% ethanol and briefly dried. The pellet is suspended in 10 ml TE containing 20 µg/ml RNAse A, (Boehringer, Mannheim) and incubated for 15 min at 37° C. The DNA is treated with nucease free pronase (1 mg/ml final concentration) (Kochlight, Coinbrook) for 1 h at 37° C.

8.5 g CsCl is dissolved in 9 ml of the DNA solution obtained, 0.2 ml 10 mg/ml ethidium bromide is added and this solution is either centrifuged in a Beckman SW41 rotor for 60 h at 33,000 rpm, or in a Beckman 50 Ti rotor for 40 h at 45,000 rpm. The DNA band is collected and the ethidium bromide is removed by multiple extraction with isopropanol equilibrated with a satured solution of NaCl in water. 5 volumes of TE are added and the DNA solution is sequentially treated with TE saturated phenol, phenol/chloroform/isoamylalcohol 25:24:1 and chloroform/isoamylalcohol 24:1. The DNA is precipitated by addition of 0.1 volume of 3M sodium acetate pH 5.2, 2.5 volumes of ethanol and an overnight incubation at −20° C. The precipitate is collected by centrifugation (1 h, 30,000× g; 4° C.), washed with 70% ethanol dried and dissolved in 400 µl TE.

Example 1.2: Partial digestion of *A. niger* N400 DNA with MboI and isolation of framents To test for the MboI concentration which gives the largest amount of DNA fragments between 13.6 and 23 kbp, 1 µg portions of *A. niger* N400 DNA are digested in the appropriate buffer recommended by the supplier with deceasing amounts of MboI (0.5–0.001 U) for 1 h at 37° C. in a volume of 10 µl. The reaction is stopped by the addition of 1 µl 0.25M EDTA, and the samples are loaded on a 0.6% agarose gel in TBE buffer, containing 1 µg/ml ethidium bromide. The MboI concentration required to give a high yield of the desired 13.6–23 kbp fragments is about 0.02 U/µg DNA. Accordingly, 200 µg of DNA in a total volume of 2 ml are digested. After 1 hr at 37° C. EDTA is added to a final concentration of 25 mM the enzyme is heat-inactivated at 65° C. for 10 min and the DNA is precipitated, washed dried and dissolved in 400 µl TE. The fragmented DNA is separated on a 0.4% preparative agarose gel at 4° C. and 40 V (3 V/cm). Fragments of the correct size are cut out of the gel and the DNA is electroeluted from the gel in a sterile dialysis tube in 2 ml TBE for 2–3 h at 100 V. The current is reversed for 30s, and the buffer containing the DNA is collected. The fragments are then concentrated by ethanol precipitation and dissolved in 100 µl TE.

Example 1.3: Preparation of vector DNA

The genomic library of *A. niger* strain N400 is constructed in the lambda vector EMBL4. The vector, which has a cloning capacity of 9–23 kbp, is described by Frischauf et al. [J. Mol. Biol. 170:827–842(1983)] and Karn et al. [Proc. Natl. Acad. Sci. USA 77:5172–76(1980)] and can be purchased from Promega Biotechnology Inc. To avoid two inserts originating from different parts of the genome being cloned into one phage, a minimal fragment length of 13.6 kbp is used for cloning.

10 µg lambda EMBL4 DNA is digested to completion with 50 units of BamHI in the buffer recommended by the supplier in a volume of 100 µl for 2 h at 37° C. The enzyme is inactivated for 10 min at 65° C. The NaCl concentration is raised to 150 mM and 50 units of SalI are added and incubation at 37° C. continues for another 2 h. After addition of EDTA to 25 mM and inactivation of the enzyme by heating for 10 min at 65° C. The solution is extracted with equal volumes of phenol (TE saturated), phenol/chloroform/isoamylalcohol 25:24:1, and chloroform/isoamylalcohol (24:1). To eliminate the small BamHI/SalI polylinker fragments, the DNA is precipitated with 0.6 volume of isopropanol after the addition of 0.1 vol. 3M sodium acetate pH 5.2. After 15 min on ice and 15 min centrifugation at 12,000× g at 4° C., the precipitate is thoroughly washed with 70% ethanol, dried and dissolved in 40 µl TE.

Example 1.4: Ligation and in vitro packaging of genomic *A. niger* N400 DNA fragments It is essential that the cos sites of the vector prepared according to example 2.3 are annealed prior to the ligation reaction. The vector in 100 mM Tris-HCl pH 7.5 and 10 mM MgCl$_2$ is heated for 10 min at 65° C. and then annealed for 1 h at 42° C. From test ligations a ratio of vector to fragments of approximately 1:1 (by weight) is found to give most recombinants. Ligation took place in 50 mM Tris HCl pH 7.5, 10 mM MgCl$_2$, 10 mM DTT and 1 mM ATP, using 9.5 µg of vector and 10 µg of DNA fragments in a total volume of 100 µl. DNA ligase (BRL) is added at a concentration of 0.5 U/µg DNA and the ligation mixture is incubated overnight at 14° C. To test for ligation a sample of the ligated DNA is run on an agarose gel. Also, as a control 0.5 µg of vector is ligated without the addition of fragments in a 5 µl volume.

The ligation mixture is concentrated by ethanol precipitation and dissolved in 20 µl TE prior to in vitro packaging.

In vitro packaging is done with Promega Packagene extracts according to the instruction of the manufacturer using 10 μl portions to package 1 μg of DNA. 1 μg of the high molecular weight control phage lambda cI857 Sam7, supplied with the extracts, is separately packaged as a control. After packaging, 500 μl of phage solution buffer (PSB) and 5 μl of chloroform are added. The recombinant phage stocks can be stored at 4° C.

Example 1.5: Titration and amplification of the *A. niger* strain N400 genomic library Cells of *E.coli* NM539 are grown on LB medium containing 0.2% maltose, 10 mM $MgSO_4$ and 1 mM $CaCl_2$ to an optical density (600 nm) of 1.0. 0.2 ml aliquots of this culture are added to 0.1 ml of an appropriate phage dilution in PSB. After adsorption of the phages for 20 min at 37° C., 3 ml 0.6% LB top-agar at 45° C. is added, the mixture is plated on LB agar plates and these are incubated overnight at 37° C. The number of plaque forming units (pfu) per ml phage suspension are $12 \times 10^5$ and $4.2 \times 10^5$ pfu/ml for two phage stocks prepared according to example 1.4. After subtracting the background which is calculated from the control ligations without fragments (17% and 40% respectively) the absolute number of recombinants is $6 \times 10^5$. The DNA contained in the recombinants is equivalent to more than 200 of the *Aspergillus niger* genomes.

To amplify the library, 80 μl aliquots of both phage stocks are used to infect *E. coli* NM539 cells which are plated in LB top-agarose on LB agar plates and then incubated overnight at 37° C. The phages are eluted from the agarose by gently shaking the plates with 5 ml PSB per plate for 1 h at room temperature. The PSB is collected, centrifuged (10 min at 6000× g) to remove bacteria and chloroform is added (0.05% final concentration). Both phage stocks, which are amplified approximately to the same extent, are then mixed (40 μl stock), titrated ($8 \times 10^9$ pfu/ml) and stored at 4° C.

Example 2

Preparation of a yeast PRB probe

Example 2.1: Preparation of the yeast Probe.

Plasmid pGP202 (deposited as DSM 7018) contains a 3.2 kb fragment of yeast DNA, that encodes the yeast PRB gene that can be conveniently excised with HindIII and SauI. This plasmid is digested with HindIII and SauI and the fragments separated on a 0.8% agarose gel. The 3.2 kb fragment is cut out and the DNA iselectroeluted. 100 ng of this fragment isnick translated with $^{32}$P-dATP as the labelled nucleotide and used immediately for either Southern or plaque lift probings.

Example 2.2: Southerns of *A. niger* DNA.

2 μg aliquots of *A. niger* DNA, prepared as described above, are digested with either BamHI or HindIII and seated on a 0.8% agarose gel. After photographing the ethidium bromide stained gel the DNA istransferred to nitrocellulose filters by capillary blotting [Southern, E. M., J. Mol. Biol. 98:503–517(1975)] and hybridised as described in example 3 with the labelled yeast PRB probe. Separate strips of nitrocellulose containing both digests are submitted to a variety of washing regimens to determine the conditions that gave the strongest signal to noise ratio. We found that a preliminary wash at 47° C. in 6×SSC followed by two room temperature washes in 2×SSC gave the best results.

Example 3

Screening of the *A. niger* N400 library with the least PRB probe

Part of the genomic library of *Aspergillus niger* strain N400 described above (Example 1) is diluted in SM and 0.1 ml portions each containing about 2000 pfu are plated. Host cells are prepared by inoculating 50 ml of LB-medium supplemented with 0.2% maltose with 0.5 ml of an overnight culture of *E.coli* NM539 in LB-medium, shaking for 4 h at 250 rpm at 37° C., followed by the addition of 0.5 ml 1M $MgSO_4$ and of 0.5 ml 0.5 $CaCl_2$. 0.2 ml aliquots of these cells are each mixed with a 0.1 ml portion of the phage suspension and incubated at room temperature for half an hour. Then 3 ml of 0.7% agarose in LM-medium at 47° C. are added, briefly vortexed and immediately plated on LM agar plates. The plates are incubated overnight at 37° C. and chilled for 2 h at 4° C.

From each plate two replicas are made according to the Benton and Davis plaque hybridization method [Benton, W. D. and Davis, R. W., Science 196:180–182(1977)]. The first filter (Schleicher and Schuell BA85) is placed on top of the plate for 1 min, the second replica for 2 min and the position of the replicas is maid using India ink. After removing the filters they are placed in a dish containing 100 ml of a denanting solution (1M NaCl, 0.5M NaOH) for 0.5 min, and then for 1 min in 100 ml neutralizing solution (0.5M Tris-HCl pH 7.5, 1.5M NaCl). The filters are tansferred to a dish containing 3×SSC, are gently rubbed with a gloved hand to remove bacterial debris and are rinsed with 3×SSC. The filters are blotted dried for 10 min at room temperature and baked on Whatman 3 MM paper in an oven at 80° C. for 2 h.

The baked filters are wetted in 3×SSC, washed in this solution for 1 h at room temperature and then transferred to a dish containing 250 ml prewarmed (65° C.) prehybridization mixture (6×SSC, 10×Denhardt's (0.2% BSA, Boehringer fraction V; 0.2% Ficoll 400, Pharmacia; 0.2% polyvinylpyrrolidone-10, Sigma), 0.1% SDS and 0.1 mg/ml sheared and freshly denatured herring sperm DNA). After 1 hr prehybridization at 65° C. in a shaking water bath the filters are washed once for half an hour in 250 ml prewarmed (65° C.) hybridization mixture, which is the same as the prehybridizaion mixture except it lacks the herring sperm DNA. Then the filters are transfered to a dish containing 150 ml of prewarmed (65° C.) hybridization mixture to which the previously labeled probe is freshly added.

After hybridising for 14 h at 65° C. the filters are washed once in 250 ml prewarmed (47° C.) hybridization mixture for half an hour at 47° C., followed by washing at room temperature in two changes of 250 ml 2×SSC, each for 45 min. The filters are dried and exposed to Kodak XAR5 film for one to three days at –70° C., using an intersifing screen.

In this way, 3 positive signals are obtained from the six plates screened. Positive plaques are punched out with a sterile Pasteur pipette by carefully positioning the plates on the autoradiogram using the ink markers. The pieces of agar containing the positive plaques are added to 1 ml of SM and 2.5 μl of chloroform is added. The phages are allowed to diffuse out of the agar for one hour at room temperature, occaissionally vortexing and then incubated overnight at 4° C. The agar and cell debris are removed by centrifugation for 5 min, 2.5 μl of chloroform is added and the phage stocks are stored at 4° C.

The positive clones are named λ1, λ2, λ4. Since phages are plated at high density, the positive plaques are purified twice by plating them at a low density and repeating the complete procedure of replica plating, hybridization and picking of positive plaques.

Example 4

Characterisation of the lambda clones
Example 4.1: Isolation of lambda DNA

To isolate DNA from the recombinant clones, phages are first amplified. For this purpose *E. coli* LE392 host cells are grown to an optical density (600 nm) of 1.0 in LB-medium supplemented with 10 mM $MgSO_4$ and 0.2% maltose. Then 50 μl of the stocks of the purified phages are separately plated as described above. After an overnight incubation at 37° C. the phages are eluted from the nonconfluent plates by sprading 5 ml of SM over the plates and incubating for two hours with gentle shaking. The eluted phages are harvested and 0.1 ml chloroform is added The mixture is briefly vortexed and cellular debris is removed by centrifugation. The supernatants are recovered, chloroform is added to 0.3% and the resulting plate lysate is stored at 4° C.

In order to obtain nearly confluent plates as starting material for the isolation of phage DNA, 10 ml portions of the plate lysates are plated with *E.coli* LE392 host cells. After overnight incubation at 37° C. the agarose top layer is scraped off from three nearly confluent plates. These layers are combined, 20 ml of SM and 0.4 ml of chloroform arm added and the resulting mixture is shaken at 37° C. for 30 min. Cellular debris and agarose are removed by centrifugation, the supernatant is recovered and its volume adjusted to 18 ml with SM. An equal volume of 2M NaCl, 20% PEG6000 (BDH Poole, GB) in SM is added and the solutions are mixed and placed on ice. After 75 min the phages are pelletted by centrifugation for 20 min at 1200× g at 4° C. The supernatant is decanted and the remaining fluid is removed with a Kleenex tissue. The pellet is resuspended in 3 ml SM and subsequently extracted with 3 ml of chloroform. The aqueous phase is treated with RNase A (67 μg/ml) and DNase I (33 μg/ml) for 20 min at 37° C. Then this mixture is extracted by adding 2 ml of phenol vortexing, adding 1 ml of chloroform, vortexing again and separating the two phases by centrifugation. The aqueous phase is extracted twice more, with 3 ml of phenol/chloroform (1:1) and 3 ml of chloroform, respectively. Then the DNA is precipitated from the aqueous phase by the sequential addition of 0.3 ml 3M sodium acetate buffer (pH 5.2) and 6 ml of ethanol. This mixture is left at 4° C. for 16 h and then the DNA is recovered by centrifugation (10 min, 12000× g, 4° C.). The pellet is dissolved in 0.4 ml of TE buffer, RNase A is added to 200 μl and incubated at 37° C. for 1 h. The DNA is precipitated, by the addition of 38 μl 3M sodium acetate buffer (pH 5.2) and 0.8 ml ethanol at 4° C. for 1 h. The DNA is recovered by centrifugation and subsequently dissolved 100 μl of TE.

Example 4.2: Restriction analysis of the *A. niger* N400 pepC clones

It is established by restriction analysis that all three phages contain inserts which are derived from the same region of the *A. niger* genome and a partial restriction map of λ1 is constructed.

2 μg of phage DNA is digested with 20 units of EcoRI in a volume of 20 μl for 1 h at 37° C. in the buffer recommended by the supplier (BRL) and then heated at 65° C. for 10 min.

The samples are run on a 0.7% agarose gel and photographed. The DNA is transferred to nitrocellulose membrane and hybridized with the labelled yeast PRB probe. It is clear from these digests that all three phages are identical containing a 12 kb and a 2.7 kb EcoRI fragment. It is also clear that the 12 kb fragment is the only fragment that hybridised to the PRB probe and henece contains most if not all of the corresponding *A. niger* gene. λ1 is chosen for further analysis.

λ1 is further digested with a variety of restriction enzymes and subjected to Southern analysis again. The smallest band that appeared to contain all of the bands hybridising to the PRB probe is a 3.2 kbp EcoRI BamHI fragment. So this is subcloned into a plasmid.

Example 5

Cloning of PEPC into a plasmid and its sequencing and characterisation

Example 5.1: Construction of pTZPEPC

λ1 DNA is incubated with the restriction enzymes BamHI and EcoRI, essentially as described above. Following extraction with chloroform, the DNA is precipitated, pelletted by centrifugation, dissolved in sample buffer and subjected to electrophoresis on a 0.6% agarose gel in 1× TBE buffer. A gel slice containing the 3.2 kbp BamHI-EcoRI fragment is recovered and the DNA is electroeluted. This is then extract with 100 μl of chloroform and ethanol precipitated and redissolved in 40 ml of TE buffer. The DNA concentration is estimated by agarose gel electrophoresis followed by visualisation of the band under UV light.

pTZ18R vector is prepared by digestion with BamHI and EcoRI, under the conditions recommended by the supplier (BRL). The DNA is extracted with phenol phenol/chloroform (1:1) and chloroform and the DNA ethanol precipitated 100 ng of each of the above fragments are ligated together in a reaction volume of 25 μl, containing the buffer recommended by BRL plus ATP (1 mM), 1.5 U of T4 DNA ligase (BRL). The reaction mixture is incubated for 16 h at 16° C. and then used transform *E.coli* DH5aF'. The cells are plated on LB agar plates containing 25 μg/ml ampicillin, 0.005% Xgal, 0.05 mM IPTG and incubated overnight at 37° C.

Several single white colonies are used to prepare overnight cultures in LB medium supplemented with 0.1% glucose and 25 mg/ml ampicillin. These cultures are used to isolate plasmid, using the miniprep method of Holmes and Quigley [Holmes, D. S. and Quigley, M., Anal.Biochem. 114:193(1981)]. The plasmids are digested with several restriction enzymes, according to the recommendations of the supplier (BRL) and in the presence of RNase A (0.5 mg/ml), and the products are analyzed on an agarose gel. Plasmids that give rise to BamHI-EcoRI and HindIII fragments of the expected size are selected and the *E.coli* cells harbouring them are kept on glycerol at −20° C. This plasmid is called pTZPEPC (deposited as DSM 7019).

Example 5.2: Nucleotide sequence of pepC

The pepC subclone, a 3.2 kbp BamHI-EcoRI fragment in the pTZ18R vector, is completely sequenced by the dideoxy-chain termination method [Sanger et al., Proc. Natl. Acad. Sci. USA 74:5463–67(1977)] using synthetic oligonucleotide primers and Sequenase (United States Biochemical Corp.).

The complete nucleotide sequence is present in the Sequence Listing. The open reading frame is identified by comparison to other known subtilisn family serine proteases and this is confirmed by transcription mapping.

Example 5.3: RNA mapping of PEPC

Total RNA is prepared from ground freeze dried mycelia that is grown on minimal media with glucose as carbon source and ammonium as nitrogen source by the method of Frederick and Kinsey [Curr. Genet. 18:53–58(1990)]. The 5' end of the messenger RNA is identified by hybridising total RNA with 32-P end labelled oligonucleotide, oligo A (complementary to nucleotides 433 to 456 of SEQ ID NO. 1) and sizing the runoff transcript produced by reverse transcriptase on a sequencing gel by comparison to sequencing reactions produced by dideoxy sequencing with the same oligonucleotide (Maniatis et al., Molecular Cloning. A Laboratory Manual. Cold Spring Harbor Laboratory, Cold Spring Harbor, N.Y., 1982). The precise splice sites of the intron are identified by cloning and sequencing a partial cDNA copy of the pepC message. First strand synthesis is performed by standard methods (Maniatis et al., op. cit.) except the priming oligonucleotide is oligo C (complementary to nucleotides 923 to 944 of SEQ ID NO. 1). This cDNA is subjected to PCR using oligos B (corresponding to nucleotides 631 to 657 of SEQ ID NO. 1) and C and cloned into pTZ18R (Note oligo B additionally has a BamHI site on its 5' end and oligo C additionally has an EcoRI site). Both strands of two independent clones are completely sequenced. The total length of the mRNA produced by the pepC gene is determined by Northern analysis using the 3.2 kb EcoRI-BamHI fragment as probe (Maniatis et al., op. cit) and is determined to be between 1.5 and 1.8 kb which corresponds to that expected from the size of the open reading frame and position of the transcription start site.

Example 6

Genomic disruption of PEPC

Example 6.1: Construction of pTZPEPCE

Plasmid pTZPEPC is digested with BamHI, treated with T4 polymerase and religated in the presence of a ten molar excess of unphosphorylated EcoRI linkers (5' GGAATTCC). Following transformation into *E.coli* the correct plasmid with EcoRI sites flanking both sides of the pepC gene is identified by miniscreen.

Example 6.2: Construction of pAXI

Plasmid pCG59D7 which can be obtained from *Escherichia coli* BJ5138/pCG59D7 (DSM 3968) is digested with XbaI and the fragment containing the whole of the *A. niger* pyrA gene is purified. This is cloned into XbaI site of pTZ18R to create plasmid pAXI (deposited as DSM 7017).

Example 6.3: Construction of pPEPCPYRA

The 4 kb XbaI fragment containing the pyrA gene is excised from pAXI and purified from the vector sequences.

2 μg of pTZPEPCE is cut with BglII according to the manufacturers recommendations and then phenol extracted, ethanol precipitated and redissolved in 20 μl of water. This DNA is then treated with bacterial alkaline phosphatase, to remove the 5' phosphate groups, as recommended by the manufacturer. The 5 kb fragment is purified from a gel.

Both of the above fragments are treated with T4 polymerase according to the manufacturers instructions and phenol extracted and ethanol precipitate. The two fragments are mixed together and ligated. After transformation of *E.coli*, the colonies carrying the correct plasmids are identified by restriction digest of mini-plasmid preparations.

pPEPCPYRA consists of pTZ18R vector containing on EcoRI fragment which carries the PEPC gene, which has the central BglII fragment, which encodes both the active site histidine and serine, replaced by an XbaI DNA fragment encoding orotidine monophosphate decarboxylase.

Example 6.4: Transformation of *A. niger*

10 μg of plasmid pPEPCPYRA is digested to completion by EcoRI. The completeness of the digest is checked by running an aliquot on a gel and the remainder of the DNA is phenol extracted, ethanol precipitated and resuspended in 20 μl of sterile water.

Conidial spores of auxotrophic *A. niger* An8 (DSM 3917) are grown for 4 days at 28° C. on complete medium until fully sporulated $2 \times 10^8$ conidiospores are used to inoculate 200 ml of minimal medium supplemented with 1 g/l arginine and uridine.

After 20 hours growth at 28° C. at 180 rpm the mycelium is harvested by filtration through Miracloth, washed twice with 10 ml 0.8M KCl, 50 mM $CaCl_2$ and resuspended in 20 ml 0.8M KCl, 50 mM $CaCl_2$, 0.5 mg/ml Novozym 234 (Novo Industries). The mixture is incubated in a shaking waterbath (30° C., 50 rpm) until sufficient protoplasts are released (detected microscopically after 90–120 min). The protoplast suspension is filtered through a glass wool plug in a funnel to remove mycelial debris. The protoplasts are pelleted by mild centrifugation (10 min, 2000 rpm) at room temperature and washed twice with 10 ml 0.8M KCl, 50 mM $CaCl_2$. The protoplasts are finally resuspended in 200–500 μl 0.8M KCl, 50 mM $CaCl_2$ to give a concentration of $1 \times 10^8$ spheroplasts per ml.

For transformation a 200 μl aliquot of the protoplast suspension is incubated with 5 μg of the EcoRI digested pPEPCPYRA 50 μl PCT (10 mM Tris-HCl pH 7.5, 50 mM $CaCl_2$, 25% PEG 6000). The incubation mixture is kept on ice for 20 min, another 2 ml of PCT are added and the mixture incubated for further 5 min at room temperature. 4 ml 0.8M KCl, 50 mM $CaCl_2$ are added and 1 ml aliquots of the final transformation solution are mixed with liquid minimal agar medium (Minimal medium +1 g/l arginine +10 g/l Bacto-Agar (Difco)), stabilised with 0.8M KCl. The mixtures am immediately poured on agar plates of the same medium and incubated at 30° C.

After 2–3 days of growth at 28° C., stable transformants appear as vigorously growing and sporulating colonies on a background growth of many hundred small, presumably abortive, transformants.

Example 6.5: Identification of gene disruptions

From the stable colonies, individual spore suspensions are made and streaked on fresh minimal plus arginine plates. Single colonies are selected and restreaked to give pure cultures. These are used to inoculate 200 ml of liquid minimal media supplemented with 1 g/l arginine. After 24 h at 30° C. shaking at 180 rpm, the mycelia is harvested on filter paper and the pad freeze dried. After drying DNA is prepared from the individual pads by grinding the pads to a fine powder with a pestle and mortar. 60 mg of this powder is resuspended in 3 ml of 1% Sodium dodecylsulfate, 0.1% Tween 80, 1M ammonium acetate by vortexing. This is heated at 65° C. for 20 min with occasional mixing. The cell debris is separated from the DNA solution by centrifugation at 15,000 rpm for 5 min. The supernatant is extracted twice with phenol, twice with chloroform and ethanol precipitated. The DNA pellet is reddisolved in 100 μl of sterile TE.

20 μl of each DNA is digested with BglII in the presence of 1 μg of RNAaseA for 1 h. This is separated on an agarose gel and transferred to nitrocellulose membrane and baked. The EcoRI fragment from pTZPEPC containing PEPC is purified, labelled by nick translation and used to probe the filters. Strains which carry a disruption of the pepC gene are easily recognized by lacking the 1.2 kb BglII hybridising fragment as well as having altered mobility of the other two flanking fragments.

One of these strains is plated on media containing uridine and 5-fluoro-orotic acid. Mutants to pyrimidine auxotrophy are identified by the stronger growth on this media and are picked off and purified by streaking for single colonies.

Example 6.6: Production of interferon in pepC⁻ A. niger strain

One of the pepC⁻ A. niger An8 strains isolated in Example 6.5 is used as a host for subsequent transformation with pyrA⁺ containing plasmids and expression cassettes containing a heterologous gene for interferon.

Conidial spores of the uridine auxotrophic pepC⁻ mutant of A. niger An8 are grown for 4 days at 28° C. in complete medium until fully sporulated. $2 \times 10^8$ conidiospores are used to inoculate 200 ml minimal medium supplemented 1 g/l arginine and uridine.

After 20 hours growth at 28° C. and 180 rpm. the mycelium is harvested by filtration through Miracloth, washed twice with 10 ml 0.8M KCl, 50 mM $CaCl_2$ and resuspended in 20 ml 0.8M KCl, 50 mM $CaCl_2$, 0.5 mg/ml Novozym 234 (Novo Industries). The mixture is incubated in a shaking waterbath (30° C., 50 rpm.) until sufficient protoplasts are released (detected microscopically after 90–120 min). The protoplast suspension is filtered through a glass wool plug in a funnel to remove mycelial debris. The protoplasts are pelleted by mild centrifugation (10 min, 2000 rpm) at room temperature and washed twice with 10 ml 0.8M KCl, 50 mM $CaCl_2$. The protoplasts are finally resuspended in 200–500 μl 0.8M KCl, 50 mM $CaCl_2$ to give a concentration of $1 \times 10^8$/ml.

For transformation a 200 μl aliquot of the protoplast suspension is incubated with 5 μg of pCG59D7 (DSM 3968) and 50 μg pGIIss-IFN AM119 or pGII-IFN AM119 DNA (both plasmids are fully disclosed in EP-Application 0 421 919), 50 μl PCT (10 mM Tris-HCl pH 7.5, 50 mM $CaCl_2$, 25% PEG 6000). The incubation mixture is kept on ice for 20 min, another 2 ml of PCT are added and the mixture incubated for further 5 min at room temperature. 4 ml 0.8M KCl, 50 mM $CaCl_2$ are added and 1 ml aliquots of the final transformation solution are mixed with liquified minimal agar medium (Minimal medium +1 g/l arginine +10 g/l Bacto-Agar (Difco)), stabilised with 0.8M KCl. The mixtures are immediately poured on agar plates of the same medium and incubated at 30° C.

After 2–3 days of growth at 28° C., stable transformants appear as vigorously growing and sporulating colonies on a background growth of many hundred small presumably abortive, transformants.

Transformants are picked and analysed for interferon expression. Interferon activity is determined according to the procedure of Armstrong (J. A. Armstrong, Appl. Microbiol. 21, 732 (1971)) using human CCL-23 cells and vesicular stomatitis virus (VSV) as the challenge virus.

Conidial spores from transformants are individually precultured into 50 ml of a preculture medium (Pectin Slow Set L (Unipectin, S A, Redon, France) 3 g/l, $NH_4Cl$ 2 g/l, $KH_2PO_4$ 0.5 g/l, NaCl 0.5 g/l, $Mg_2SO_4.7H_2O$ 0.5 g/l, $Ca_2SO_4.2H_2O$ 0.5 g/l, pH 7.0, 1% arginine). The preculture is incubated for 72 hours at 250 rpm and 28° C. 10% of the preculture is used to inoculate 50 ml of main culture medium (Soybean fluor 20 g/l, pectin Slow Set 5 g/l, 1% arginine). The culture is grown up for 72–96 hours at 250 rpm and 28° C.

At various times (every 20 hours) samples are taken, the cells are pelleted by centrifugation and broken by freezedrying and dry grinding. Supernatant and cell extracts are both tested for inteferon activity as described (supra). The bulk of the interferon activity is found secreted into the medium in transformants carrying pGIIss-IFN AM119 while in transformants carrying pGII-IFN AM119 it is mainly in the cell extract.

Example 7

Overexpression of pepC in A. niger

Example 7.1: Overexpression of multiple copies

A. niger An8 is transformed with 1 μg pAXI 10 μg pTZPEPC to yield uridine photohphs. Colonies are purified and DNA prepared as described above. Southern blots using the EcoRI-BamHI fragment of pTZPEPC showed that some transformants have a single copy of pTZPEPC integrated into their genome whereas others have upto and above 10 extra copies in their genome. There strains produced correspondingly more proteolytic activity and are stable mitotically.

Example 7.2: Overexpression of pepC from gene fusions

The plasmid pGW1100 (deposited as DSM 5747) is cut with BamHI and SacI. The 1.2 kbp fragment encompassing the pyruvate kinase promoter and 5' end is purified, treated with the T4 polymerase and cloned into the unique BamHI site of pTZPEPC at the 5' end of the pepC clone, that is also blunt-ended with T4 polymerase and treed with alkaline phosphatase.

The correct plasmids are identified by miniscreening and one is chosen and transformed into a dut- ung- E.coli, strain BW313. This is superinfected with M13K07 to yield single stranded uracil-substituted DNA from the plasmid.

Oligonucleotide 1 (depicted under SEQ ID NO. 3) consists of 37 nucleotides. The first 19 nucleotides are complementary to the first 19 nucleotides of the pepC open reading frame and the last 18 are complementary to the last 18 nucleotides before the ATG of the pyruvate kinase gene. For the in vitro mutagenesis of this plasmid 5 pM of oligonucleotide 1 are phosphorylated at the 5' end with 100 pM ATP by treating the oligo with 10 U of T4 polynucleotide kinase in 50 μl kinase buffer as recommended by the supplier. The reaction is terminated by heating at 65° C. for 10 min.

0.2 pM uracil-containing single-stranded DNA is mixed with 0.5 pM phosphorylated oligonucleotide 1 in 20 mM Tris-HCl pH7.5, 10 mM $MgCl_2$, 25mM NaCl in a final volume of 10 μl. The mixture is incubated at 65° C. for 5 min, slowly cooled to room temperature over 60 min and placed on ice for 15 min. Then 2 μl 500 uM dNTP's, 1.5 μl 10 mM ATP, 1 ml T7 DNA polymerase (1.2 U/μl Pharmacia) and 1 ul T4 DNA ligase (12 U/μl BRL) are added to the mixture and this polymerisation mixture is incubated for 15 min at 37° C. The reaction is terminated by heating at 65° C. for 5 min and aliquots used to transform E. coli DH5αF'.

The correct plasmids are identified by digesting miniplasmid preparations. 3 are chosen and the EcoRI fragment is completely sequenced using synthetic oligonucleotides. One plasmid which contains a perfect fusion of the pyruvate kinase promoter to the pepC open reading frame, which is called pPKIPEPCA, is used with pAXI to cotransform A. niger An8 to uridine prototrophy.

The presence of the pki-pepC fusion is confined by making DNA from individual purified transformants and using it for Southern analysis using probes from pki and pepC. Strains with one or more copy of this gene fusion integrated into their genome are shown to produce more proteolytic activity when the cells are grown rapidly on glucose as C source.

Example 8

Expression of pepC in other organisms: Expression in yeast

The plasmid pPKIPEPCA is in vitro mutagenised with the two synthetic oligonucleotides shown in the sequence listing under SEQ ID NO. 4 and 5. The former one engineers an EcoRI site just before the ATG of pepC and the other loops out the whole of the intron. This creates a plasmid pPKIPEPCB who's sequence is confirmed by complete sequencing.

The 2.8 kb EcoRI-BamHI fragment that starts just before the ATG of pepC and finishes after the pepC terminator is purified and ligated together with the 520 bp BamHI-EcoRI fragment of pFBY129 (deposited as DSM 7016), that contains the yeast GAL10 promoter, into the SnaBI site of yeast two micron based vector pFBY25 (deposited as DSM 7020). A correct plasmid is identified by restriction digests.

This plasmid, pFBY138, is transformed into yeast and shown to produce pepC protein when the gene fusion is induced by galactose.

Example 9

Isolation of a DNA probe for the screening for A. niger subtilisin-like serine proteases Example 9.1: Design of degenerate PCR (polymerase chain reaction) primers The polymerase chain reaction (Saiki et al., Science 230:1350–1354 (1985)) is used to isolate probes for this screening. The two regions containing the active site residues histidine and serine, respectively, are well conserved among different proteases of the subtilisin-class. A consensus amino acid sequence is derived for each of these regions and the DNA sequences capable of coding for these two amino acid sequences are deduced. To reduce the level of degeneracy two primers for each of the conserved regions are designed. PCRoligo 1 and PCRoligo 2 (shown in SEQ ID NO. 8 and 9, respectively) correspond to the His active site region and PCRoligo 3 and PCRoligo 4 (shown in SEQ ID NO. 10 and 11, respectively) correspond to the Ser active site region. To facilitate later subcloning of the PCR products, PCRoligos 1 and 2 contain a BamHI and PCRoligos 3 and 4 an EcoRI restriction site near their 5' ends as well.

Example 9.2: Amplification of A. niger genomic DNA

A. niger genomic DNA is isolated as described in Example 1. Four amplification reactions are carried out using a pairwise combination of the four PCR oligos described above. The reaction mixture for the polymerase chain reaction contains 100 ng total genomic A. niger DNA, 100 pmol of each primers, 10 mM TRIS-HCl, 50 mM KCl, 1.5 mM MgCl2, 1 mg/ml gelatine, (pH 8.3) and 5 units of Taq DNA polymerase in a total of 50 µl. The DNA is denatured at 94° C. for 30 seconds then the primers are annealed at 42° C. for 40 seconds and the extension step is done at 72° C. for 60 seconds. These three steps are then repeated 40 times.

Example 9.3: Isolation and characterisation of the PCR Products

The products of the amplification reactions are separated on a 1% agarose gel and the DNA fragments isolated from the gel by electroelution as described above. The isolated fragments (200–300 ng) are extracted with phenol and then with chloroform and precipitated with ethanol. After centrifugation the DNA pellets are dried and then dissolved in 10 µl TE buffer. This DNA is then digested with 10 units of BamHI and EcoRI restriction enzymes in a volume of 20 µl for 1 h at 37° C. in the buffer recomended by the supplier (BRL). Following extraction with phenol and chloroform and precipitation with ethanol the digested DNA is pelleted, dried and redissolved in 10 µl TE buffer. The DNA concentration is estimated by agarose gel electrophoresis followed by visualisation of the DNA band under UV light.

pTZ18R vector is prepared by digestion with BamnHI and EcoRI under the conditions recommended by the supplier (BRL) and then extracted and ethanol precipitated as described above.

100 ng of the isolated PCR fragments are ligated together with 100 ng of the prepared pTZ18R vector described above in a volume of 20 µl with 1 unit of T4 DNA ligase. The buffer conditions used are those suggested by the supplier (BRL). After incubating of the reaction mixture at 16° C. for 16 h, it is used to transform E. coli DH5αF' strain. Cells are plated on LB agar plates containing 25 µg/ml ampicillin, 0.005% Xgal, 0.05 mM IPTG and incubated overnight at 37° C.

Several single white colonies are used to prepare overnight cultures in 5 ml LB medium supplemented with 0.1% glucose and 25 µg/ml ampicillin. These cultures are used to isolate plasmid DNA, using the miniprep method of Holmes and Quigley (Holmes, D. S. and Quigley, M., Anal Biochem. 114:193 (1981). The plasmids are digested with BamHI and EcoRI restriction enzymes according to the recommendations of the supplier (BRL). Plasmids that contain fragments are further analysed.

Inserts of selected plasmids are sequenced by the dideoxy-chain termination method (Sanger et al., Proc.Natl. Acad. Sci. USA 74:5463–67 (1977)) using synthetic oligonucleotide primers and Sequenase (United States Biochemical Corp.).

Example 9.4: Computer analysis of the sequences of the PCR products

The nucleotide sequences of the above inserts are compared to all the DNA sequences in the combined GenBank and EMBL databases. One of them, which shows strong homology to the DNA sequences coding for subtilisin type protases is chosen as probe, and called PCR-probe, for subsequent screening of the A. niger genomic library. The sequence of this fragment (without the PCR primers) is that between nucleotides 1474 and 2020 in the sequence shown in SEQ ID NO. 6.

Example 10

Screening of the A. niger N400 library with PCR probe

Filters for plaque hybridization of the genomic library of Aspergillus niger strain N400 described above (Example 1) are prepared and prehybridized according to Example 3.

After hybridizing for 14–16 h at 65° C. the filters are washed once in 250 ml 2×SSC, 0.1 % SDS for half an hour at room temperature followed by washing at room temperature in two changes of 250 ml 0.2×SSC, 0.1% SDS each for 20 min, and finally twice in 250 ml 0.2×SSC, 0.1% SDS at 65° C. each for 20 min. The filters are dried and exposed to Kodak XAR5 film for one to three days at −70° C., using an intensifying screen.

In this way, 5 positive signals are obtained from the six plates screened. Positive plaques are punched out with a sterile Pasteur pipette by carefully positioning the plates on the autoradiogram using the ink markers. The pieces of agar containing the positive plaques are added to 1 ml of SM and 2.5 µl of chloroform is added. The phages are allowed to diffuse out of the agar for one hour at room temperature, occassionally vortexing and then incubated overnight at 4° C. The agar and cell debris are removed by centrifugation for 5 min, 2.5 µl of chloroform is added and the phage stocks are stored at 4° C.

The positive clones are named λa, λb, λc, λd and λe. Since phages are plated at high density, the positive plaques are purified twice by plating them at a low density and repeating the complete procedure of replica plating, hybridization and picking of positive plaques.

Example 11

Characterisation of the lambda clones
Example 11.1: Isolation of lambda DNA and Restriction analysis of the *A. niger* N400 pepD clones Lambda DNA is isolated as described in Example 4.1.

It is established by restriction analysis that all five phages λa to λe contain inserts which are derived from the same region of the *A. niger* genome and a partial restriction map of that genomic region is constructed.

2 μg of phage DNA is digested with 20 units of EcoRI or BamHI in a volume of 20 μl for 1 h at 37° C. in the buffer recommended by the supplier (BRL) and then heated at 65° C. for 10 min. The samples are run on a 0.7% agarose gel and photographed. The DNA is transferred to nitrocellulose membrane and hybridized with the labelled PCR probe.

It is clear from these digests that the 5 phages contain an approximately 5.5 kb overlapping region that hybridised to the PCR-probe and hence contains most if not all of the corresponding *A. niger* gene. A 6.0 kbp long BamHI fragment contained this region and is chosen for further analysis.

Example 12

Cloning of PEPD into a plasmid and its sequencing and characterisation
Example 12.1: Construction of pTZPEPD The 6.0 kb BamHI fragment is incubated with the restriction enzyme HindIII. Following extraction with chloroform, the DNA is precipitated, pelletted by centrifugation, dissolved in sample buffer and subjected to electrophoresis on a 0.6% agarose gel in 1× TBE buffer. A gel slice containing the 3.0 kbp BamHI-HindIII fragment is recovered and the DNA is electroeluted. This is then extracted with 100 μl of chloroform and ethanol precipitated and redissolved in 40 ml of TE buffer. The DNA concentration is estimated by agarose gel electrophoresis followed by visualisation of the band under UV light.

pTZ18R vector is prepared by digestion with BamHI and HindIII, under the conditions recommended by the supplier (BRL). The DNA is extracted with phenol, phenol/chloroform (1:1) and chloroform and the DNA ethanol precipitated.

100 ng of each of the above fragments am ligated together in a reaction volume of 25 μl, containing the buffer recommended by BRL plus ATP (1 mM), 1.5 U of T4 DNA ligase (BRL). The reaction mixture is incubated for 16 h at 16° C. and then used transform *E.coli* DH5αF'. The cells are plated on LB agar plates containing 25 μg/ml ampicillin, 0.005% Xgal, 0.05 mM IPTG and incubated overnight at 37° C.

Several single white colonies are used to prepare overnight cultures in LB medium supplemented with 0.1% glucose and 25 mg/ml ampicillin. These cultures are used to isolate plasmid, using the miniprep method of Holmes and Quigley [Holmes, D. S. and Quigley, M., Anal.Biochem. 1 14:193(1981)]. The plasmids are digested with several restriction enzymes, according to the recommendations of the supplier (BRL) and in the presence of RNase A (0.5 mg/ml), and the products are analyzed on an agarose gel. Plasmids that give rise to BamHI-HindIII fragments of the expected size are selected and the *E.coli* cells harbouring them are kept on glycerol at −20° C. This plasmid is called pTZPEPD (deposited as DSM 7409).

Example 12.2: Nucleotide sequence of pepD

The pepD subclone, a 3.0 kbp BamHI-HindIII fragment in the pTZ18R vector, is completely sequenced by the dideoxy-chain termination method [Sanger et al., Proc. Natl. Acad. Sci. USA 74:5463–67(1977)] using synthetic oligonucleotide primers and Sequenase (United States Biochemical Corp.).

The complete nucleotide sequence is present in the Sequence Listing under SEQ ID NO. 6. The open reading frame is identified by comparison to other known subtilisn family serine proteases and this is confirmed by transcription mapping.

Example 12.3 RNA mapping of PEPD

Total RNA is prepared from ground freeze dried mycelia that is grown on minimal media with glucose as carbon source and ammonium as nitrogen source by the method of Frederick and Kinsey [Curr. Genet. 18:53–58(1990)]. The 5' end of the messenger RNA is identified by hybridising total RNA with 32-P end labelled oligonucleotide, oligo A (complementary to nucleotides 851 to 876 of SEQ ID NO. 6) and sizing the runoff transcript produced by reverse transcriptase on a sequencing gel by comparison to sequencing reactions produced by dideoxy sequencing with the same oligonucleotide (Maniatis et al., Molecular Cloning. A Laboratory Manual. Cold Spring Harbor Laboratory, Cold Spring Harbor, N.Y., 1982). The precise splice sites of the introns are identified by cloning and sequencing a partial cDNA copy of the pepD message. First strand synthesis is performed by standard methods (Maniatis et al., op. cit.) except the priming oligonucleotide is oligo C (complementary to nucleotides 1914 to 1941 of SEQ ID NO. 6). This cDNA is subjected to PCR using oligos B (corresponding to nucleotides 1102 to 1129 of SEQ ID NO. 6) and C and cloned into pTZ18R. Note that nucleotides 1107–1109 (GGT) are replaced by ATC in oligoB thus creating new BamHI site. Similarly, nucleotides 1932 (A) and 1935 (A) were replaced by G and T, respectively, in oligoC thus creating a new HindIII site. Both strands of two independent clones are completely sequenced. The total length of the mRNA produced by the pepD gene is determined by Northern analysis using the 3.0 kb EcoRI-HindIII fragment as probe (Maniatis et al., op. cit) and is determined to be between 1.4 and 1.7 kb which corresponds to that expected from the size of the open reading frame and position of the transcription start site.

Example 13

Genomic disruption of PEPD
Example 13.1: Construction of pPEPCPYRA

The 4 kb XbaI fragment containing the pyrA gene is excised from pAXI (DSM 7017) and purified from the vector sequences.

2 μg of pTZPEPD is cut with NheI and NcoI according to the manufacturers recommendations and then phenol extracted, ethanol precipitated and redissolved in 20 μl of water. This DNA is then treated with bacterial alkaline phosphatase, to remove the 5' phosphate groups, as recommended by the manufacturer. The 5.3 kb fragment lacking the 0.6 kbp NheI-NcoI fragment that contains the His and Ser active sites is purified from a gel.

Both of the above fragments are treated with T4 polymerase according to the manufacturers instructions and phenol extracted and ethanol precipitated. The two fragments are mixed together and ligated. After transformation of *E.coli*, the colonies carrying the correct plasmids are identified by restriction digest of mini-plasmid preparations.

pPEPDPYRA consists of pTZ18R vector containing a BamHI-HindIII fragment which carries the pepD gene, which has the central NheI-NcoI fragment, which encodes the His and Ser active sites, replaced by an XbaI DNA fragment encoding orotidine monophosphate decarboxylase.

Example 13.4: Transformation of *A. niger*

10 μg of plasmid pPEPDPYRA is digested to completion by EcoRI. The completeness of the digest is checked by running an aliquot on a gel and the remainder of the DNA is phenol extracted, ethanol precipitated and resuspended in 20 μl of sterile water.

Conidial spores of auxotrophic *A. niger* An8 (DSM 3917) are grown for 4 days at 28° C. on complete medium until fully sporulated $2 \times 10^8$ conidiospores are used to inoculate 200 ml of minimal medium supplemented with 1 g/l arginine and uridine.

After 20 hours growth at 28° C. at 180 rpm the mycelium is harvested by filtration through Miracloth, washed twice with 10 ml 0.8M KCl, 50 mM $CaCl_2$ and resuspended in 20 ml 0.8M KCl, 50 mM $CaCl_2$, 0.5 mg/ml Novozym 234 (Novo Industries). The mixture is incubated in a shaking waterbath (30° C., 50 rpm) until sufficient protoplasts are released (detected microscopically after 90–120 min). The protoplast suspension is filtered through a glass wool plug in a funnel to remove mycelial debris. The protoplasts are pelleted by mild centrifugation (10 min, 2000 rpm) at room temperature and washed twice with 10 ml 0.8M KCl, 50 mM $CaCl_2$. The protoplasts are finally resuspended in 200–500 μl 0.8M KCl, 50 mM $CaCl_2$ to give a concentration of $1 \times 10^8$ spheroplasts per ml.

For transformation a 200 μl aliquot of the protoplast suspension is incubated with 5 μg of the EcoRI digested pPEPDPYRA 50 μl PCT (10 mM Tris-HCl pH 7.5, 50 mM $CaCl_2$, 25% PEG 6000).The incubation mixture is kept on ice for 20 min, another 2 ml of PCT are added and the mixture incubated for further 5 min at room temperature. 4 ml 0.8M KCl, 50 mM $CaCl_2$ are added and 1 ml aliquots of the final transformation solution are mixed with liquid minimal agar medium (Minimal medium+1 g/l arginine+10 g/l Bacto-Agar (Difco)), stabilised with 0.8M KCl. The mixtures are immediately poured on agar plates of the same medium and incubated at 30° C.

After 2–3 days of growth at 28° C., stable transformants appear as vigorously growing and sporulating colonies on a background growth of many hundred small, presumably abortive, transformants.

Example 13.5: Identification of gene disruptions

From the stable colonies, individual spore suspensions are made and streaked on fresh minimal plus arginine plates. Single colonies are selected and restreaked to give pure culture. These are used to inoculate 200 ml of liquid minimal media supplemented with 1 g/l arginine. After 24 h at 30° C. shaking at 180 rpm, the mycelia is harvested on filter paper and the pad freeze dried. After drying DNA is prepared from the individual pads by grinding the pads to a fine powder with a pestle and mortar. 60 mg of this powder is resuspended in 3 ml of 1% Sodium dodecylsulfate, 0.1% Tween 80, 1M ammonium acetate by vortexing. This is heated at 65° C. for 20 min with occasional mixing. The cell debris is separated from the DNA solution by centrifugation at 15,000 rpm for 5 min. The supernatant is extracted twice with phenol twice with chloroform and ethanol precipitated. The DNA pellet is reddisolved in 100 μl of sterile TE.

20 μl of each DNA is digested with NheI and NcoI in the presence. of 1 μg of RNAaseA for 1 h. This is separated on an agarose gel and transferred to nitrocellulose membrane and baked. The HindIII-BamHI fragment from pTZPEPD containing PEPD is purified, labelled by nick translation and used to probe the filters. Strains which carry a disruption of the pepD gene are easily recognized by lacking the 0.6 kb NheI-NhoI hybridising fragment as well as having altered mobility of the other two flanking fragments.

One of these strains is plated on media containing uridine and 5-fluoro-orotic acid. Mutants to pyrimidine auxotrophy are identified by the stronger growth on this media and are picked off and purified by streaking for single colonies.

Example 13.6: Production of interferon in pepD⁻ *A. niger* strain

One of the pepD⁻ *A. niger* An8 strains isolated in Example 6.5 is used as a host for subsequent transformation with pyrA⁺ containing plasmids and expression cassettes containing a heterologous gene for interferon.

Conidial spores of the uridine auxotrophic pepD⁻ mutant of *A. niger* An8 are grown for 4 days at 28° C. in complete medium until fully sporulated $2 \times 10^8$ conidiospores are used to inoculate 200 ml minimal medium supplemented 1 g/l arginine and uridine.

After 20 hours growth at 28° C. and 180 rpm. the mycelium is harvested by filtration through Miracloth, washed twice with 10 ml 0.8M KCl, 50 mM $CaCl_2$ and resuspended in 20 ml 0.8M KCl, 50 mM $CaCl_2$, 0.5 mg/ml Novozym 234 (Novo Industries). The mixture is incubated in a shaking waterbath (30° C., 50 rpm.) until sufficient protoplasts arm released (detected microscopically after 90–120 min). The protoplast suspension is filtered through a glass wool plug in a funnel to remove mycelial debris. The protoplasts are pelleted by mild centrifugation (10 min, 2000 rpm) at room temperature and washed twice with 10 ml 0.8M KCl, 50 mM $CaCl_2$. The protoplasts are finally resuspended in 200–500 μl 0.8M KCl, 50 mM $CaCl_2$ to give a concentration of $1 \times 10^8$/ml.

For transformation a 200 μl aliquot of the protoplast suspension is incubated with 5 μg of pCG59D7 (DSM 3968) and 50 μg pGIIss-IFN AM119 or pGII-IFN AM119 DNA (both plasmids are fully disclosed in EP-Application 0 421 919), 50 μl PCT (10 mM Tris-HCl pH 7.5, 50 mM $CaCl_2$, 25% PEG 6000). The incubation mixture is kept on ice for 20 min, another 2 ml of PCT are added and the mixture incubated for further 5 min at room temperature. 4 ml 0.8M KCl, 50 mM $CaCl_2$ are added and 1 ml aliquots of the final transformation solution are mixed with liquified minimal agar medium (Minimal medium+1 g/l arginine+10 g/l Bacto-Agar (Difco)), stabilised with 0.8M KCl. The mixtures are immediately poured on agar plates of the same medium and incubated at 30° C.

After 2–3 days of growth at 28° C., stable transformants appear as vigorously growing and sporulating colonies on a background growth of many hundred small, presumably abortive, transformants.

Transformants are picked and analysed for interferon expression. Interferon activity is determined according to the procedure of Armstrong (J. A. Armstrong, Appl. Microbiol. 21, 732 (1971)) using human CCL-23 cells and vesicular stomatitis virus (VSV) as the challenge virus.

Conidial spores from tranformants are individually precultured into 50 ml of a preculture medium (Pectin Slow Set L (Unipectin, S A, Redon, France) 3 g/l , $NH_4Cl2$ g/l, $KH_2PO_4$ 0.5 g/l, NaCl 0.5 g/l, $Mg_2SO_4.7H_2O$ 0.5 g/l, $Ca_2SO_4.2H_2O$ 0.5 g/l, pH 7.0, 1% arginine). The preculture is incubated for 72 hours at 250 rpm and 28° C. 10% of the preculture is used to inoculate 50 ml of main culture medium (Soybean fluor 20 g/l, pectin Slow Set 5 g/l, 1% arginine). The culture is grown up for 72–96 hours at 250 rpm and 28° C.

At various times (every 20 hours) samples are taken, the cells are pelleted by centrifugation and broken by freezedrying and dry grinding. Supernatant and cell extracts are both tested for inteferon activity as described (supra). The bulk of the interferon activity is found secreted into the medium in transformants carrying pGHIIss-IFN AM119 while in transformants carrying pGII-FFN AM119 it is mainly in the cell extract.

Example 14

Overexpression of pepD in A. niger

Example 14.1: Overexpression of multiple copies

A. niger An8 is transformed with 1 μg pAXI plus 10 μg pTZPEPD to yield uridine photohphs. Colonies are purified and DNA prepared as described above. Southern blots using the HindIII fragment of pTZPEPD showed that some transformants have a single copy of pTZPEPD integrated into their genome whereas others have upto and above 10 extra copies in their genome. These strains produced correspondingly more proteolytic activity and are stable mitotically.

Example 14.2: Overexpression of pepD from gene fusions

A gene fusion is constructed which consists of the A. niger pyruvate kinase promoter region and of the coding and terminator regions of the A. niger pepD gene. The fusion is constructed by recombinant PCR (R. Higuchi: Recombinant PCR pp 177–183 in Innis et al., (eds) PCR Protocols, Academic Press, Inc. (1990)). Four oligonucleotide primers are designed of which fusoligo 1, 2, and 3 are shown in SEQ ID NO. 12, 13 and 14, respectively, whereas fusoligo 4 is complementary to the sequence between nucleotides 2858 and 2874 in SEQ ID 1. Fusoligo 1 hybridises to the pki promoter 0.75 kbp upstream of the ATG start codon. Fusoligo 2 and 3 are partially overlapping on complementary strands, both contain sequences of the pki promoter immediately upstream from the ATG translation start codon, the ATG codon itself and also sequences of the pepD coding region immediately downstream of the ATG codon. Fusoligo 4 hybridises to the pepD gene downstream region, 0.65 kbp downstream of the translation stop site. Two PCR reactions are performed essentially as described above. In the first, a 0.75 kbp pki promoter fragment is amplified using fusoligo 1 and 2 and PGW1100 (DSM 5747) as template. In the second a 2.0 kb fragment that containes the pepD coding and termination regions is amplified using fusoligo 3 and 4 and pTZPEPD as template. The amplification products are purified from agarose gel, combined, denatured and reannealed. The two fragments form homo- and also heteroduplexes during the reannealing reaction because of their overlapping ends due to fusoligo 2 and 3. This annealed mixture is then reamplified by PCR using the two "outside" primers (fusoligo 1 and 4). The product of this reaction is isolated, purified and subcloned into a plasmid vector.

The correct plasmids are identified by digesting miniplasmid preparations. 2 are chosen and the insert is completely sequenced using synthetic oligonucleotides. One plasmid which contains a perfect fusion of the pyruvate kinase promoter to the pepD open reading frame, which is called pPKIPEPCA, is used with pAXI to cotransform A. niger An8 to uridine prototrophy.

The presence of the pki-pepD fusion is confirmed by making DNA from individual purified transformants and using it for Southern analysis using probes from pki and pepD. Strains with one or more copy of this gene fusion integrated into their genome are shown to produce more proteolytic activity when the cells are grown rapidly on glucose as C source.

Example 15

Expression of pepD in other organisms: Expression in yeast

The plasmid pTZPEPD is cut by EcoRI, blunt ended with T4 polymerase and religated thus removing the EcoRI site from the polylinker region. The resulting plasmid is then is vitro mutagenised with the four synthetic oligonucleotides oligoyeast 1, 2, 3, and 4 shown in the sequence listing under SEQ ID NO. 15, 16, 17 and 18, respectively. Oligoyeast1 engineers an EcoRI site just upstream of the ATG of pepD and the other three loop out the whole of each of the 3 introns. This creates plasmid pTZPEPDa who's sequence is confirmed by complete sequencing.

The 2.2 kb EcoRI-BamHI fragment that starts just before the ATG of pepD and finishes after the terminator region is purified and ligated together with the 520 bp BamHI-EcoRI fragment of pFBY129 (DSM 7016), that contains the yeast GAL10 promoter, into the SnaBI site of yeast two micron based vector pFBY25 (DSM7020). A correct plasmid is identified by restriction digests. This plasmid, pGAL10PEPD, is transformed into yeast and shown to produce pepD protein when the expression of the gene fusion is induced by galactose.

Deposition of Microorganisms

Following microorganisms are deposited under the Budapest treaty with the Deutsche Sammlung von Mikroorganismen und Zellkulturen, Mascheroder Weg 1b, D-3300 Braunschweig:

| Microorganism/Plasmid | Depos. Date | Deposition No. |
| --- | --- | --- |
| E. coli DH5αF'/pGW1100 | Jan. 18, 1990 | DSM 5747 |
| E. coli BJ5183/pCG59D7 | Feb. 2, 1987 | DSM 3968 |
| A. niger An8 | Dec. 11, 1986 | DSM 3917 |
| E. coli DH5αF'/pTZPEPC | March 30, 1992 | DSM 7019 |
| E. coli DH5αF'/pGP202 | March 30, 1992 | DSM 7018 |
| E. coli DH5αF'/pFBY129 | March 30, 1992 | DSM 7016 |
| E. coli DH5αF'/pAXI | March 30, 1992 | DSM 7017 |
| E. coli DH5αF'/pFBY25 | March 30, 1992 | DSM 7020 |
| E. coli DH5αF'/pTZPEPD | Jan. 19, 1993 | DSM 7409 |

We claim:

1. A DNA molecule comprising a DNA sequence selected from the group consisting of the pepC coding region shown in SEQ ID NO. 1 and the pepD coding region shown in SEQ ID NO. 6.

2. A hybrid vector comprising a DNA molecule according to claim 1.

3. A hybrid vector according to claim 2 in which a DNA sequence coding for an *Aspergillus niger* serine protease of the subtilisin-type is functionally linked with regulatory elements suitable for the expression of such a DNA sequence in a suitable host cell.

4. A hybrid vector according to claim 3 in which a DNA sequence coding for an *Aspergillus niger* serine protease of the subtilisin-type is functionally linked with regulatory elements suitable for the expression of such a DNA sequence in an Aspergillus strain.

5. A hybrid vector according to claim 4 comprising a promoter homologous to the desired DNA sequence coding for an *Aspergillus niger* serine protease of the subtilisin-type.

6. A hybrid vector according to claim 3 comprising a promoter heterologous to the desired DNA sequence coding for an *Aspergillus niger* serine protease of the subtilisin-type.

7. A host transformed with a hybrid expression vector comprising a DNA sequence according to claim 3 functionally linked with regulatory elements suitable for the expression of the DNA sequence in said host.

8. A transformed host according to claim 7 which is an *Aspergillus niger* strain.

9. A transformed host according to claim 8 which is an *Aspergillus niger* strain transformed with a hybrid expression vector comprising a promoter homologous to the DNA sequence coding for an *Aspergillus niger* serine protease of the subtilisin-type.

10. A transformed host according to claim 8 which is an *Aspergillus niger* strain transformed with a hybrid expression vector comprising a promoter heterologous to the DNA sequence coding for an *Aspergillus niger* serine protease of the subtilisin-type.

11. A process for the preparation of a transformed host according to claim 7 comprising transforming a suitable host with a hybrid expression vector comprising a DNA sequence coding for an *Aspergillus niger* serine protease of the subtilisin-type functionally linked with regulatory elements suitable for the expression of the DNA sequence in said host.

12. A process for the preparation of an *Aspergillus niger* serine protease of the subtilisin-type, said process comprising culturing a suitable host which is transformed with a hybrid expression vector comprising a DNA sequence according to claim 1 which codes for an *Aspergillus niger* serine protease of the subtilisin-type functionally linked with regulatory elements suitable for the expression of the DNA sequence in said suitable host.

13. A process for the preparation of a DNA molecule according to claim 1 comprising culturing a host cell transformed with a DNA molecule coding for an *Aspergillus niger* serine protease of the subtilisin-type and isolating said DNA molecule from the host cell.

* * * * *